United States Patent [19]
Boger et al.

[11] Patent Number: 4,812,442
[45] Date of Patent: Mar. 14, 1989

[54] TRIPEPTIDE RENIN INHIBITORS

[75] Inventors: Joshua S. Boger, Westfield, N.J.; Ben E. Evans, Landsdale; Mark G. Bock, Hatfield, both of Pa.

[73] Assignee: Merck & Co., Inc., Rahway, N.J.

[21] Appl. No.: 45,941

[22] Filed: May 4, 1987

Related U.S. Application Data

[63] Continuation-in-part of Ser. No. 886,487, Jul. 16, 1986, which is a continuation-in-part of Ser. No. 758,625, Jul. 24, 1985, abandoned, which is a continuation-in-part of Ser. No. 614,881, May 29, 1984, abandoned.

[51] Int. Cl.$^4$ .................. A61K 34/43; C07K 5/06; C07K 5/08; C07D 241/04; C07D 265/30; C07D 211/30; C07D 211/70; C07D 263/02; C07D 233/54; C07D 207/04
[52] U.S. Cl. ........................ 514/18; 514/19; 548/569; 548/342; 548/215; 548/950; 544/400; 544/159; 544/168; 546/247; 546/335; 546/336; 530/331
[58] Field of Search .................. 530/329, 331; 514/19, 514/18; 548/569, 342, 215, 950; 544/400, 159, 168; 546/247, 335, 336

[56] References Cited

U.S. PATENT DOCUMENTS 4,638,047  1/1987  Szelke et al. .................. 530/332

Primary Examiner—Delbert R. Phillips
Attorney, Agent, or Firm—Hesna J. Pfeiffer; Frank S. Chow

[57] ABSTRACT

Enzyme tripeptides of the formula:

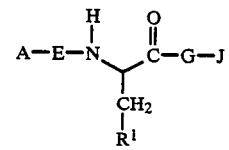

and analogs thereof which inhibit renin and are useful for treating various forms of renin-associated hypertension, hyperaldosteronism and congestive heart failure; compositions containing these renin-inhibitory peptides, optionally with other antihypertensive agents; and methods of treating hypertension, hyperaldosteronism or congestive heart failure or of establishing renin as a causative factor in these problems employing the novel tripeptides.

8 Claims, No Drawings

TRIPEPTIDE RENIN INHIBITORS

CROSS REFERENCE TO RELATED APPLICATIONS

This application is a continuation-in-part of U.S. patent application Ser. No. 886,487, filed July 16, 1986, which in turn is a continuation-in-part of U.S. patent application Ser. No. 758,625, filed July 24, 1985, now abandoned, which in turn is a continuation-in-part of U.S. patent application Ser. No. 614,881, filed May 29, 1984, now abandoned.

The present invention is concerned with novel peptides which inhibit the proteolytic enzyme, renin, with pharmaceutical compositions containing the novel peptides of the present invention as active ingredients, with methods of treating renin-associated hypertension, hyperaldosteronism, and congestive heart failure, with diagnostic methods which utilize the novel peptides of the present invention, and with methods of preparing the novel peptides of the present invention.

BACKGROUND OF THE INVENTION

Renin is an endopeptidase (molecular weight about 40,000) produced and secreted by the juxtaglomerular cells of the kidney, which cleaves its plasma substrate, angiotensinogen, specifically at the 10, 11 peptide bond, i.e., between Leu 10 and Leu 11 in the equine substrate, as described by Skeggs et al, *J. Exper. Med.* 1957, 106, 439, or between the Leu 10 and Val 11 in the human renin substrate, as elucidated by Tewksbury et al., *Circulation* 59, 60, Supp. II: 132, Oct. 1979 Renin cleaves angiotensinogen to split off the decapeptide, angiotensin I, which is converted by angiotensin-converting enzyme to the potent pressor substance angiotensin II. Thus, the renin-angiotensin system plays an important role in normal cardiovascular homeostasis and in some forms of hypertension.

Inhibitors of angiotensin I converting enzyme have proven useful in the modulation of the renin-angiotensin system and consequently, specific inhibitors of the limiting enzymatic step that ultimately regulates angiotensin II production, the action of renin on its substrate, have also been sought as effective investigative tools and as therapeutic agents in the treatment of hypertension and congestive heart failure.

Renin antibody, pepstatin, phospholipids, and substrate analogs, including tetrapeptides and octa- to tridecapeptides, with inhibition constants ($K_i$) in the $10^{-3}$ to $10^{-6}$M region, have been studied.

Umezawa et al., in *J. Antibiot.(Tokyo)* 23: 259–262, 1970, reported the isolation of a peptide, pepstatin, from actinomyces that was an inhibitor of aspartyl proteases such as pepsin, cathepsin D, and renin. Gross et al., *Science* 175:656, 1972, reported that pepstatin reduces blood pressure in vivo after the injection of hog renin into nephrectomized rats, but pepstatin has not found very wide application as an experimental agent because of its limited solubility and its inhibition of a variety of other acid proteases in addition to renin.

Many efforts have been made to prepare a specific renin inhibitor based on pig renin substrate analogy, which as been shown to correlate well with and predict human renin inhibitor activity. The octapeptide amino acid sequence extending from histidine-6 through tyrosine-13

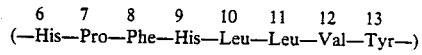

(—His—Pro—Phe—His—Leu—Leu—Val—Tyr—)

has been shown to have kinetic parameters essentially the same as those of the full tetradecapeptide renin substrate.

Kokubu et al., *Biochem. Pharmacol.*, 22, 3217–3223, 1973, synthesized a number of analogs of the tetrapeptide found between residues 10 to 13, but while inhibition could be shown, inhibitory constants were only of the order of $10^{-3}$M. Analogs of a larger segment of renin substrate were synthesized, Burton et al., *Biochemistry* 14: 3892–3898, 1975, and Poulsen et al., *Biochemistry* 12: 3877–3882, 1973, but a lack of solubility and weak binding (large inhibitory constant) have proven to be major obstacles to obtaining effective renin inhibitors.

Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counter-productive. Other approaches to increasing solubility have had limited success.

Modifications designed to increase binding to renin have also been made, but here too, with mixed results.

Powers et al., in *Acid Proteases, Structure, Function and Biology*, Plenum Press, 1977, 141–157, have suggested that in pepstatin, statine occupies the space of the two amino acids on either side of the cleavage site of a pepsin substrate, and Tang et al., in *Trends in Biochem. Sci.*, 1:205–208 (1976) and *J. Biol. Chem.*, 251:7088–94, 1976, have proposed that the statine residue of pepstatin resembles the transition state for pepsin hydrolysis of peptide bonds. Inhibitors of renin which contain the amino acid statine have been disclosed in the following: Veber et al, U.S. Pat. No. 4,384,994; European Published Application No. 77 029; Evans et al, U.S. Pat. No. 4,397,786; Veber et al, EP-A No. 77 028; Boger et al, *Nature*, 1983, 303, 81–84; U.S. Pat. No. 4,470,971; EP-A Nos. 114 993 and 157 409; U.S. Pat. No. 4,485,099; Matsueda et al, EP-A No. 128 762, 152 255; Morisawa et al., EP-A No. 186 977; Riniker et al, EP-A No. 111 266; Bindra et al, EP-A No. 155 809; Stein et al, Fed. Proc. 1986, 45, 869; and German Patent Application DE No. 3438-545-A.

Renin inhibitors containing other peptide bond isosteres, including a reduced carbonyl peptide bond isostere are disclosed by M. Szelke et al, in work described in published European Patent Application Nos. 45 665, 104 041, U.S. Pat. No. 4,424,207, and in PCT Int. Appl. No. WO 84 03,044; *Nature*, 299, 555 (1982); *Hypertension*, 4, Supp. 2, 59, 1981; British Pat. No. 1,587,809; and in *Peptides, Structure and Function: Proceedings of the Eighth American Peptide Symposium*, ed. V. J. Hruby and D. H. Rich, p. 579, Pierce Chemical Co., Rockford, Ill., 1983, where substitution at the Leu-Leu site of renin cleavage by isosteric substitution, resulted in compounds with excellent potency. Other peptide bond isosteres have been disclosed in Buhlmayer et al in EP-A Nos. 144 290 and 184 550; Hester et al, EP-A No. 173 481; Raddatz, EP-A No. 161 588; Dann et al, *Biochem. Biophys. Res. Commun.* 1986, 134, 71–77; Fuhrer et al, EP-A No. 143 746; Kamijo et al, EP-A No. 181 110; Thaisrivongs et al, *J. Med. Chem.*, 1985, 28, 1553–1555; Ryono et al., EP-A No. 181 071; and Evans et al, U.S. Pat. No. 4,609,641.

Renin inhibitors with non-peptide C-termini are disclosed in European Published Application Nos. 172 346 and 172 347; Evans et al, *J. Med. Chem.*, 1985, 28, 1755–1756; and Bock et al in *Peptides, Structure and Function: Proceedings of the Ninth American Peptide Symposium*, ed. C. M. Deber et al, pp 751–754, Pierce Chemical Co., Rockford, Ill., 1985.

Peptide aldehyde renin inhibitors are disclosed by Kokubu et al, *Hypertension*, 1985, 7, Suppl. I, p. 8–10; Matsueda et al, *Chemistry Letters*, 1985, 1041–1044; European Published Application Nos. 128 762 and 152 255. Peptide glycol inhibitors of renin are reported by Hanson et al in *Biochem. Biophys. Res. Commun.* 1985, 132, 155–161.

The renin inhibitors cited above in large part comprise peptide-based inhibitors in which a sequence of the type: . . . A-B-D-E-F-G-J-K-L . . . , where G is a peptide bond mimic and A,B,D,E,F,J,K, and L may individually be absent or may represent naturally-occuring or modified amino acids. Typical sequences of this type include:

$$\overset{7}{\text{. . . BOC}}-\overset{8}{\text{Pro}}-\overset{9}{\text{Phe}}-\overset{10}{\text{His}}-\overset{11}{\text{Sta}}-\overset{12}{\text{Leu}}-\text{Phe. . .},$$

$$\text{or . . . BOC}-\overset{8}{\text{Phe}}-\overset{9}{\text{His}}-\overset{10}{\text{Sta}}-\overset{11}{\text{Leu. . .}},$$

where the N-terminus typically comprises an amino acid protecting group such as BOC or CBZ, and the N-terminal amino acids are Pro-Phe-His or Phe-His.

It was an object of this invention to prepare lower molecular weight peptides which have enhanced biological potency in inhibiting the renin enzyme. It was also an object to prepare peptides wherein a stabilizing peptide bond mimic is substituted for the 10- and 11-position amino acids in the analogous substrate. It was a further object of this invention to prepare peptides comprising modifications at the C- and N-terminii of a shortened peptide. It was an additional object of this invention to prepare peptides in which polar and/or charged groups (+and/or −) have been selectively introduced at strategic positions in order to constructively alter the physical properties of these peptides. It was still a further object of this invention to prepare novel peptides which more effectively inhibit the activity of renin and thereby are more useful antihypertensive agents, and compounds useful in treating hyperaldosteronism and congestive heart failure.

DETAILED DESCRIPTION OF THE INVENTION

The present invention discloses renin-inhibitory tripeptides of the formula:

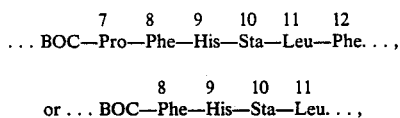

(I)

wherein: A is hydrogen or

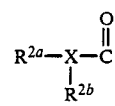

where X is $$-\text{O}-;\ -\overset{|}{\text{O}}-\overset{|}{\text{CH}}-;\ -\overset{|}{\text{CH}}-\overset{|}{\text{O}}-;\ -\overset{|}{\text{CH}}-;\ -\overset{|}{\text{NH}}-\overset{|}{\text{CH}}-;\ \text{or}$$

$$-\overset{|}{\text{S}}-\overset{|}{\text{CH}}-;\ \text{and}$$

$R^{2a}$ and $R^{2b}$ are independently hydrogen, W—$(CH_2)_n$— or W—$(CH_2)_m$—CH=CH—$(CH_2)_p$, where W is hydrogen; $C_1$–$C_4$-alkyl; aryl, wherein aryl is unsubstituted or mono-, di- or trisubstituted phenyl or naphthyl, where the substituent(s) is/are independently selected from the group consisting of $C_1$–$C_8$-alkyl, amino, mono- or di-$C_1$–$C_4$-alkylamino, amino-$C_1$–$C_4$-alkyl, hydroxy-$C_1$–$C_4$-alkyl, mono- or di-$C_1$–$C_4$-alkylamino-$C_1$–$C_4$-alkyl, guanidyl, guanidyl-$C_1$–$C_4$-alkyl, hydroxyl, $C_1$–$C_4$-alkoxy, $CF_3$, halo, CHO, $CO_2H$, $CO_2$—$C_1$–$C_4$-alkyl, $CO_2$—$C_1$–$C_4$-alkoxy, $NR^5R^6$, and $N(R^5)_3 \oplus A \ominus$, wherein $R^5$ and $R^6$ are independently hydrogen, unsubstituted or monosubstituted $C_1$–$C_4$-alkyl, where the substituent is amino, $C_1$–$C_4$-alkylamino, di-$C_1$–$C_4$-alkylamino, hydroxyl, $C_1$–$C_4$-alkoxy or $N(C_1$–$C_4$-alkyl$)_3 \oplus A \ominus$; and $A \ominus$ *is a counterion selected from the group consisting of single negatively-charged ions, such as chloride, bromide, hydroxide and acetate*; or unsubstituted or mono-, di- or trisubstituted $C_3$–$C_7$-cycloalkyl, wherein the substituent(s) is/are independently selected from the group consisting of $C_1$–$C_8$-alkyl, trifluoromethyl, hydroxy, $C_1C_4$-alkoxy, and halo; n is 0 to 5; and m and p are independently 0 to 2; except that where X is —O—, only one of $R^{2a}$ or $R^{2b}$ is present; E is absent; or

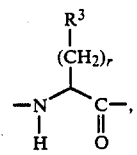

where r is 1 to 4; and $R^3$ is hydrogen; $C_1$–$C_4$-alkyl; aryl, as defined above; aryl-$C_1$–$C_4$-alkyl; or indolyl; $R^1$ is hydrogen; $C_1$–$C_4$-alkyl; hydroxy-$C_1$–$C_4$-alkyl; aryl, as defined above; indolyl; 4-imidazolyl; amino-$C_2$–$C_4$-alkyl;

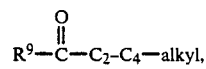

wherein $R^9$ is hydrogen, $C_1$–$C_4$-alkyl, hydroxy or $C_3$–$C_7$-cycloalkyl; guanidyl-$C_2$–$C_3$-alkyl; or methylthiomethyl; G is

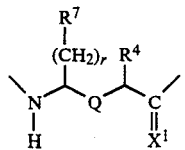

where $X_1$ is O or HH; $R_4$ is hydrogen or

wherein $R^3$, $R^9$ and r are as defined above; $R^7$ is $C_3$-$C_6$-alkyl; aryl, as defined above; or unsubstituted or mono-, di- or trisubstituted $C_3$-$C_7$-cycloalkyl, wherein the substituent(s) is/are independently selected from the group consisting of $C_1$-$C_4$-alkyl, trifluoromethyl, hydroxy, $C_1$-$C_4$-alkoxy, and halo; and Q is

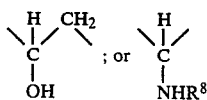

wherein $R^8$ is H; $C_1$-$C_4$-alkyl; formyl; $C_1$-$C_4$-alkanoyl; aroyl; $C_1$-$C_4$-alkoxy-carbonyl; aryloxycarbonyl; or aryl $C_1$-$C_4$-alkoxycarbonyl; or

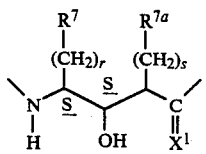

where s is 0 to 4; $R^{7a}$ is hydrogen; $C_1$-$C_8$-alkyl; $C_2$-$C_8$-alkenyl; mono- or disubstituted $C_2$-$C_8$-alkyl, wherein the substituent(s) is/are on the final 1 and/or 2 carbon atoms of the alkyl chain and is/are independently selected from the group consisting of hydroxy, carboxy, $CO_2$-$C_1$-$C_4$-alkyl, amino, mono-, di-, or tri-$C_1$-$C_4$-alkylamino, guanidyl, and $NR^5R^6$ and $N(R^5)_3 \oplus A\ominus$, where $R^5$, $R^6$ and $A\ominus$ are as above; aryl, as defined above; unsubstituted or mono-, di- or trisubstituted $C_3$-$C_7$-cycloalkyl, wherein the substituent(s) is/are independently selected from the group consisting of $C_1$-$C_4$-alkyl, trifluoromethyl, hydroxy, $C_1$-$C_4$-alkoxy, and halo; $R^7$, $X^1$ and r are as defined above; and wherein the second alternate G definition of the above formula has a 2S or 2R, 3S, 4S configuration; and J is —Y—($CH_2$)$_n$—$R^{10}$, where Y is —NH—, —O— or $N(CH_2)_n$—$R^{10}$, provided that when $X^1$ is HH, Y is —O—; $R^{10}$ is hydrogen; hydroxy; $C_1$-$C_4$-alkyl; $C_3$—$C_7$-cycloalkyl; $C_1$-$C_4$-alkyl-$SO_2OH$; aryl, as defined above; $NR^{11a}R^{11b}$, wherein $R^{11a}$ and $R^{11b}$ are independently hydrogen; unsubstituted or mono-substituted $C_1$-$C_4$-alkyl, wherein the substituent is carboxy, sulfo or hydroxy; monosubstituted $C_2$-$C_4$-alkyl, wherein the substituent is on the terminal carbon and is amino or mono- or di-$C_1$-$C_4$-alkylamino; aryl, as defined above; aryl-$C_1$-$C_4$-alkyl; Het; or Het-$C_1$-$C_4$-alkyl, wherein Het is an unsubstituted or mono- or disubstituted 5- or 6-membered heterocyclic ring or benzofused 5- or 6-membered heterocyclic ring, where the one or two heteroatoms are independently selected from the group consisting of N, O, S, NO, SO, $SO_2$ or quaternized N, and the substituent(s) is/are independently selected from the group consisting of hydroxyl, thiol, $C_1$-$C_6$-alkyl, $CF_3$, $C_1$-$C_4$-alkoxy, halo, aryl, aryl-$C_1$-$C_4$-alkyl, amino, mono- or di-$C_1$-$C_4$-alkylamino, amino-$C_1$-$C_4$-alkylamino, amino-$C_1$-$C_4$-alkyl, hydroxy-$C_1$-$C_4$-alkyl, di-$C_1$-$C_4$-alkylamino-$C_1$-$C_4$-alkyl, guanidyl, guanidyl-$C_1$-$C_4$-alkyl, CHO, $CO_2H$, $CO_2$-$C_1$-$C_4$-alkyl, $NR^5R^6$, and $N(R^5)_3 \oplus A\ominus$ wherein $R^5$, $R^6$ and A are as defined above; $N(R^{11a})_3 \oplus A\ominus$, where $R^{11a}$ and $A\ominus$ are as defined above; guanidino-$C_2$-$C_4$-alkyl; or guanidyl; except that when n is 0, $R^{10}$ cannot be hydroxy or $NR^{11a}R^{11b}$, and when n is 0 and $R^{10}$ is hydrogen, G cannot be 4-amino-3-hydroxy-6-methylheptanoic acid (statine) when E is $\alpha$-amino-$\beta$-phenyl-propionic acid (phenylalanine);

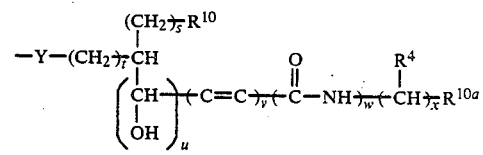

where $R^{10a}$ is independently one of the definitions of $R^{10}$,

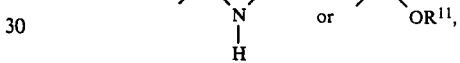

where $R^{11}$ is hydrogen or $C_1$-$C_3$-alkyl; x is 1 to 4; t, u, v and w are independently 0 or 1, provided that w is not 1 when v is 0 and when t is 0, u, v, w and x are not simultaneously 0; and Y, $R^4$, $R^{10}$ and s are as defined above;

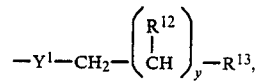

where $Y^1$ is —NH—, —N—$C_1$-$C_4$-alkyl— or —O—; provided that when $X^1$=HH, $Y^1$ is —O—; y is 1 to 4; $R^{12}$ is hydrogen; hydroxy; $NH_2$; $N(C_1$-$C_4$-alkyl$)_2$; $NH(C_1$-$C_4$-alkyl); guanidyl; or $N(C_1$-$C_4$-alkyl$)_3 \oplus A\ominus$, wherein $A\ominus$ is as defined above; provided that at least one $R^{12}$ is other than hydrogen; and $R^{13}$ is $C_1$-$C_4$-alkyl; $C_3$-$C_7$-cycloalkyl; aryl, as defined above, with the substituent(s) on the substituted aryl also alternatively selected from the group consisting of $\alpha$-amino-carboxy-$C_1$-$C_4$-alkyl, $\alpha$-aminocarboxy-$C_1$-$C_4$-alkyl ester or amide, and carboxy-$C_1$-$C_4$-alkyl ester or amide; $CO_2H$; $CO_2$-$C_1$-$C_4$-alkyl; $NR^5R^6$, wherein $R^5$ and $R^6$ are defined as above; sulfo; or Het, as defined above;

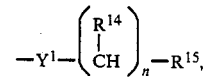

where $R^{14}$ is hydrogen, $CO_2H$, $CO_2$-$C_1$-$C_4$-alkyl or $NR^5R^6$, wherein $R^5$ and $R^6$ are as defined above; $R^{15}$ is $CO_2H$; $CO_2$-$C_1$-$C_4$-alkyl; $NR^5R^6$, wherein $R^5$ and $R^6$ are as defined above; sulfo; or aryl, as defined above, with the substituent(s) on the substituted aryl also alternatively being selected from the group consisting of α-aminocarboxy-$C_1$–$C_4$-alkyl, α-amino-carboxy-$C_1$–$C_4$-alkyl ester or amide, and carboxy-$C_1$–$C_4$-alkyl ester or amide; and $Y^1$ and n are defined as above; except that when n is 1, neither $R^{14}$ nor $R^{15}$ is $NR^5R^6$ and when n is 2, 3, 4 or 5, the $R^{14}$ on the carbon adjacent $Y^1$ cannot be $NR^5R^6$;

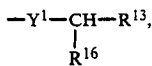

where $R^{16}$ is $CO_2H$ or $CO_2$-$C_1$–$C_4$-alkyl; and $Y^1$ and $R^{13}$ are as defined above, except that $R^{13}$ in this formula cannot be $NR^5R^6$; or

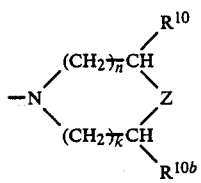

where Z is NH, $NR^{10}$, $NR^{11a}$, $R^{11b}$, O, S, SO, $SO_2$ or $CHR^{10}$, wherein $R^{10}$ is as defined above; k is 1 to 5; $R^{10b}$ is independently one of the definitions of $R^{10}$; Het, as defined above; or Het substituted by a 5- or 6- membered heterocyclic ring or benzofused heterocyclic ring, where the one or two heteroatoms are independently selected from N, O and S; and pharmaceutically-acceptable salts thereof.

In the peptides of the present invention, the A, E, G and J components have asymmetric centers and occur as racemates, racemic mixtures and as individual diastereomers, with all isomeric forms generally being included in the present invention. In particular, asymmetric carbon atoms in the G substituent has either an S or an R configuration, except as noted in one alternate definition of G above, and all other asymmetric carbon atoms have an S configuration, with preferred chiralities indicated in the following further description.

When any variable (e.g., aryl, $R^3$, $R^4R^5$, $R^7$, $R^{12}$, $R^{14}$, etc.) occurs more than one time in any constituent or in formula I, its definition on each ocurrence is independent of its definition every other occurrence.

As used herein, "alkyl" is intended to include both branched- and straight-chain saturated aliphatic hydrocarbon groups having the specified number of carbon atoms (Me is methyl, Et is ethyl); "alkoxy" represents an alkyl group of indicated number of carbon atoms attached through an oxygen bridge; and "$C_3$–$C_7$-cycloalkyl" is intended to include cycloalkyl groups, such as cyclopropyl, cyclobutyl, cyclopentyl, cyclohexyl (Cyh) and cycloheptyl. "Alkanoyl" is intended to include those alkylcarbonyl groups of specified number of carbon atoms, which are exemplified by formyl, acetyl, propanoyl and butanoyl; "alkenyl" is intended to include alkenyl groups of either a straight- or branched-configuration and one unsaturation, such as ethenyl, propenyl, butenyl, pentenyl, and the like; and "arylalkyl" represents aryl groups as herein defined which are attached through a straight- or branched-chain alkyl group of specified number of carbon atoms, such as, for example, benzyl, phenethyl, 3,3-diphenylpropyl, 3-indolymethyl, and the like. "Halo", as used herein, means fluoro, chloro, bromo and iodo, and "counterion" is used to represent a small, single negatively-charged specie, such as chloride, bromide, hydroxide, acetate, perchlorate, and the like.

As used herein, with exceptions as noted, "aryl" is intended to mean phenyl (Ph) or naphthyl, which is optionally-substituted by from one- to three-members independently selected from the group consisting of amino, mono- or di- $C_1$–$C_4$-alkylamino, amino-$C_1$–$C_4$-alkyl, hydroxy-$C_1$–$C_4$-alkyl, $C_1$–$C_4$-dialkylamino-$C_1$–$C_4$-alkyl, guanidyl, guanidyl-$C_1$–$C_4$-alkyl, hydroxyl, $C_1$–$C_4$-alkoxy, $CF_3$, halo, CHO, $CO_2H$, $CO_2R^7$, $NR^5R^6$ wherein $R^7$, $R^5$ and $R^6$ are as defined above, or $N(R^5)_3 \ominus A\oplus$, wherein $R^5$ is as defined above and $A\oplus$ is a counterion, as defined herein. "Aroyl" is intended to include those aryl-carbonyl groups which are exemplified by benzoyl and naphthoyl.

The term "Het", as used herein, represents a 5- or 6-membered heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Fully-saturated heterocyclic substituents are preferred and those in which nitrogen is the heteroatom are also preferred, with those containing a single nitrogen atom being particularly preferred. In the case of a heterocyclic ring containing one or more nitrogen atoms, the point of attachment may be at one of the nitrogen atoms, or at any carbon atom. Examples of such heterocyclic elements include piperidyl, piperidinyl, piperazinyl, 2-oxopiperazinyl, pyrryl, pyrrolinyl, 4-piperidonyl, pyrrolidinyl, pyrazolyl, pyrazolinyl, pyrazolidinyl, imidazolyl, imidazolinyl, imidazolidinyl, pyridyl, pyrazinyl, pyrimidinyl, pyridazinyl, oxaolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, benzothiazolyl, benzoxazolyl, furyl, thienyl, benzothienyl, morpholinyl, thiamorpholinyl, thiamorpholinyl sulfoxide, and thiamorpholinyl sulfone. The heterocyclic moiety is further optionally-substituted by from one- to three- members independently selected from the group consisting of hydroxyl, thiol, $C_1$–$C_6$-alkyl, $CF_3$, $C_1$–$C_4$-alkoxy, halo, aryl, aryl-$C_1$–$C_4$-alkyl, amino, mono- or di-$C_1$–4-alkylamino, amino-$C_1$–$C_4$-alkylamino, amino-$C_1$–$C_4$-alkyl, hdroxy-$C_1$–$C_4$-alkyl, $C_1$–$C_4$-dialkylamino-$C_1$–$C_4$-alkyl, guanidyl, guanidyl $C_1$–$C_4$-alkyl, hydroxyl, CHO, $CO_2H$, $CO_2R^7$, $NR^5R^6$, wherein $R^7$, $R^5$ and $R^6$ are as defined above, or $N(R^5)_3 \ominus A\oplus$, wherein $R^5$ is as defined above and $A\oplus$ is a counterion, as defined herein, with aryl-$C_1$–$C_4$-alkyl being preferred.

The following additional abbreviations have also been used herein:

| Abbreviated Designation | Amino Acid/Residue |
|---|---|
| ACHPA | (3S,4S)—4-amino-5-cyclohexyl-3-hydroxypentanoic acid |
| AHPPA | (3S,4S)—4-amiono-3-hydroxy-5-phenylpentanoic acid |
| Ala | D- or L-alanine |
| Arg | D- or L-arginine |
| Cal (Cha) | β-cyclohexylalanine |
| Cys | D- or L-cysteine |

| Abbreviated Designation | |
|---|---|
| Gly | glycine |
| His | D- or L-histidine |
| HomoPhe | homologated L-phenylalanine |
| HomoTrp | homologated L-tryptophan |
| HomoTyr | homologated L-tyrosine |
| Ile | L-isoleucine |
| Leu | D- or L-leucine |
| Lys | D- or L-lysine |
| Met | D- or L-methionine |
| Nle | L-norleucine |
| Nva | L-norvaline |
| Orn | D- or L-ornithine |
| Phe | D- or L-phenylalanine |
| Pro | D- or L-proline |
| Sar | sarcosine (N—methylglycine) |
| Ser | D- or L-serine |
| Sta | statine, (3S,4S)—4-amino-3-hydroxy-6-methylheptanoic acid |
| Thr | D- or L-threonine |
| Trp | D- or L-tryptophan |
| Tyr | D- or L-tyrosine |
| Val | L-valine |
| Protecting Group | |
| BOC (Boc) | t-butyloxycarbonyl |
| BOM | benzyloxymethyl |
| CBZ (Cbz) | benzyloxycarbonyl(carbobenzoxy) |
| DNP | 2,4-dinitrophenyl |
| IPOC | isopropoxycarbonyl |
| OMe | methyl ether (methoxy), except when it immediately follows an amino acid residue abbreviation and it represents methyl ester |
| OEt | ethoxy, except when it immediately follows an amino acid residue abbreviation and it represents ethyl ester |
| Activating Group | |
| HBT (HOBt) | 1-hydroxybenzotriazole hydrate |
| OMs | methane sulfonyloxy |
| Condensing Agent | |
| DCCI (DCC) | dicyclohexylcarbodiimide |
| DPPA | diphenylphosphorylazide |
| Reagent | |
| AMP | 4-aminomethylpyridine |
| (BOC)$_2$O | di-t-butyl dicarbonate |
| DEAD | diethyl azodicarboxylate |
| TEA | triethylamine |
| TFA | trifluoroacetic acid |
| Coupling Reagents | |
| BOP reagent | benzotriazol-1-yloxytris(dimethylamino)phosphonium hexafluorophosphate |
| BOP—Cl | bis(2-oxo-3-oxazolidinyl)phosphinic cloride |
| DSO | N,N'—disuccinimidyl oxalate |
| Solvent | |
| A | conc. ammonium hydroxide |
| AcOH (HOAc) | acetic acid |
| C | chloroform |
| DMF | dimethylformamide |
| EtOAc (E) | ethyl acetate |
| Et$_2$O | ether |
| M | methanol |
| P | pyridine |
| THF | tetrahydrofuran |
| W | water |
| Coreactants | |
| Glu | glutamic acid |
| Pic | picolinic acid |
| Tau | taurine |

The novel renin inhibitory peptides of the present invention may alternately be described in terms of common amino acid components and closely-related analogs thereof, in accordance with the following formula, analogous to formula I:

$$A\text{-}E\text{-}B\text{-}G\text{-}J \qquad (II).$$

wherein A, G and J are as defined under Formula I; B is Absent, Ala, Leu, Ser, Thr, Phe, Tyr, Trp, His, Lys, Orn, Arg, Cys, Nle, Nva, or Met; and E is Absent, Ala, Leu, Phe, HomoPhe, BisHomoPhe, Tyr, HomoTyr, Trp, or HomoTrp.

In terms of substrate analogy, a unique aspect and essential feature of the present invention is the substitution of the G-component for the double amino acid sequence, Leu$^{10}$-Leu$^{11}$ in the endogenous pig renin substrate, or Leu$^{10}$-Val$^{11}$ in the endogenous human renin substrate 7   8   9   10  11  12  13
(Pro Phe His Leu Val Ile His), which substitution for both amino acids at the cleavage site rather than just one is believed to result in an improved substrate analogy and better fit to the renin enzyme in linear extent, due to the greater linear extent of the component as compared to a single leucine component.

In additinn to an increase in metabolic stability achieved with the substitution of statine analogs/residue (particularly ACHPA), and in the shortening of the peptide chain, the novel peptides of the instant invention successfully use hydrophilic and/or hydrophobic groups strategically and comprise simplified N- and C-terminii, preferably with the elimination of α-amino acids following ACHPA at the C-terminus of these peptides. These peptides are of lower molecular weight and different structure, with an enhanced potency and duration of action, than known peptides of this class.

It will be understood that closely-related analogs of the above common amino acids, for example, aliphatic amino acids in addition to Ala, Val, Leu, and Ile, such as α-aminobutyric acid (Abu), and substituted phenyl derivatives of Phe, are included in the broad description of the novel inhibitory peptides of the present invention represented by Formulae I and II and related definitions.

Preferred renin-inhibitory peptides are those wherein J is

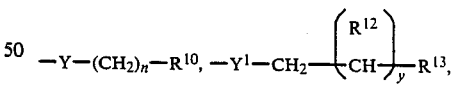

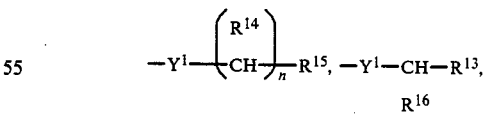

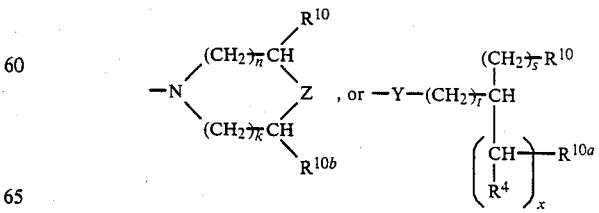

and X$^1$ is 0. More particularly preferred peptides are those wherein X$^1$ is O, R$^{7a}$ is C$_3$-C$_6$-alkyl; aryl, as defined above; or unsubstituted or mono-, di- or trisubstituted $C_3$–$C_7$-cycloalkyl, wherein the substituent(s) is-/are independently selected from the group consisting of $C_1$–$C_4$-alkyl, trifluoromethyl, hydroxy, $C_1$–$C_4$-alkoxy, and halo; and E is

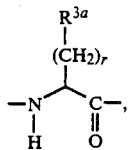

where $R^{3a}$ is aryl, as defined above, or indolyl.

Representative preferred renin-inhibitory peptides of the present invention include the following:

BOC-Phe-His-2-butyl-ACHPA-isoamyl amide
BOC-Phe-His-2-isopropyl-ACHPA amide
BOC-Phe-His-AHPPA-NHCH(i-butyl)CH$_2$NHCH$_2$(-pyrid-2-yl)
BOC-Phe-His-NHCH(CH$_2$cyclohexyl)CH(OH)CH$_2$CH$_2$OCH$_3$
BOC-Phe-His-NHCH(CH$_2$cyclohexyl)CH(OH)CH$_2$CH$_2$OEt
BOC-Phe-His-NHCH(CH$_2$cyclohexyl)CH(OH)CH$_2$CH$_2$O-CH(CH$_3$)$_2$
BOC-Phe-His-(2-isobutyl)ACHPA-OEt
BOC-Phe-His-(2-isoamyl)ACHPA-OEt
BOC-Phe-His-ACHPA-piperidine amide
BOC-Phe-His-ACHPA-(3,5-dimethyl)piperidine amide
BOC-Phe-His-ACHPA-(2-hydroxymethyl)piperidine amide
BOC-Phe-His-ACHPA-(2-carboxy)piperidine amide
BOC-Phe-His-ACHPA-Pic-OEt
BOC-Phe-His-ACHPA-pyrrolidine amide
BOC-Phe-His-NHCH[CH$_2$(4-methylenecyclohexyl)]CH(OH)CH$_2$CO-piperidine amide
BOC-Phe-His-NHCH[CH$_2$(4-methylcyclohexyl)]CH(OH)CH$_2$CO-piperidine amide
BOC-Phe-His-NHCH[CH$_2$(4-methoxycyclohexyl)]CH(OH)CH$_2$CO-piperidine amide
BOC-Phe-His-NHCH[CH$_2$(4-chlorocyclohexyl)]CH(OH)CH$_2$CO-piperidine amide
BOC-Phe-His-(2-cyclohexylmethyl)ACHPA-piperidine amide
BOC-Phe-His-(2-allyl)ACHPA-piperidine amide
BOC-Phe-His-(2-propyl)ACHPA-OEt
BOC-Phe-His-N-(2-allyl)-ACHPA-NH(2-pentyl)
BOC-Phe-His-(2-isobutyl)ACHPA-piperidine amide
BOC-Phe-His-NHCH[CH$_2$(4-hydroxycyclohexyl)]CH(OH)CH$_2$CO$_2$-Et
BOC-Phe-His-NHCH[CH$_2$(4-methylcyclohexyl)]CH(OH)CH$_2$CO$_2$CH(CH$_3$)$_2$
BOC-Phe-His-NHCH[CH$_2$(4-oxocyclohexyl)]CH(OH)CH$_2$CO$_2$Et
IPOC-Phe-His-NHCH[CH$_2$(4-methylcyclohexyl)]CH(OH)CH$_2$CONH (2-pentyl)
IPOC-Phe-His-(2-isobutyl)ACHPA-NH-(2-butyl)
IPOC-Phe-His-(2-isobutyl)ACHPA-piperidine amide
IPOC-Phe-His-(2-isobutenyl)ACHPA-piperidine amide
BOC-Phe-His-ACHPA-morpholine amide
BOC-Phe-His-ACHPA-2,6-dimethylmorpholin-4-yl amide
BOC-Phe-His-ACHPA-(4-thiamorpholine) amide
BOC-Phe-His-ACHPA-(4-thiamorpholine-1,1-dioxide) amide
BOC-Phe-His-ACHPA-(4-thiamorpholine-1-oxide) amide
BOC-Phe-His-ACHPA-(2,6-dimethylthiamorpholin-4-yl) amide
BOC-Phe-His-ACHPA-N(CH$_2$CH$_2$)$_2$NH
BOC-Phe-His-ACHPA-N[CH$_2$CH(CH$_3$)]$_2$NH
BOC-Phe-His-ACHPA-N(CH$_2$CH$_2$)$_2$N-Et
[BOC-Phe-His-ACHPA-N(CH$_2$Ch$_2$)$_2$NEt$_2$]$^\oplus$Cl$^\ominus$
BOC-Phe-His-ACHPA-(2-hydroxymethyl)pyrrolidine amide
BOC-Phe-His-ACHPA-3-thiazolidine amide
BOC-Phe-His-ACHPA-(3-thiazolidinesulfoxide) amide
BOC-Phe-His-ACHPA-(3-thiazolidine sulfone) amide
BOC-Phe-His-ACHPA-[(3-benzyl)imidazolidine]amide
BOC-Phe-His-ACHPA-(3-oxazole) amide
BOC-Phe-His-ACHPA-azepine amide
BOC-Phe-His-ACHPA-azetidine amide
BOC-Phe-His-ACHPA-2,6-dihydroxy-4-pyrimidyl amide
BOC-Phe-His-ACHPA-NH(pyrazin-2-yl)
BOC-Phe-His-ACHPA-3-methyl-2-pyridyl amide
BOC-Phe-His-ACHPA-2-ethyl-6-methylphenyl amide
BOC-Phe-His-ACHPA-NH(thiazol-2-yl)
BOC-Phe-His-ACHPA-NH(2,2,6,6-tetramethylpiperidin-4-yl)
BOC-Phe-His-ACHPA-NH(piperidin-4-yl)
BOC-Phe-His-ACHPA-NH-(1-ethylpiperidin-4-yl)
[BOC-Phe-His-ACHPA-NH(1,1-diethylpiperidonium-4-yl)$\oplus$Cl$^\ominus$
BOC-Phe-His-ACHPA-NH(1-phenylpiperidin-4-yl)
[BOC-Phe-His-ACHPA-NH(1-methyl-1-phenylpiperidonium-4-yl)]$\oplus$Cl$^\ominus$
BOC-Phe-His-ACHPA-NHCH$_2$CH$_2$(1-ethylpiperidin-4-yl)
[BOC-Phe-His-ACHPA-NHCH$_2$CH$_2$(1,1-diethylpiperidin-4-y)]$^{61}$Cl$^\ominus$
BOC-Phe-His-ACHPA-NHCH$_2$CH$_2$(piperidin-1-yl)
[BOC-Phe-His-ACHPA-NHCH$_2$Ch$_2$(2-methylpiperidin-1-yl)]$\oplus$Cl$^\ominus$
BOC-Phe-His-ACHPA-NHCH$_2$CH$_2$(morpholin-4-yl)
[BOC-Phe-His-ACHPA-NHCH$_2$CH$_2$(4-ethylmorpholinium-4-yl)$\oplus$Cl$^\ominus$
BOC-Phe-His-ACHPA-NHCH$_2$CH$_2$(CH$_3$)$_2$
BOC-Phe-His-ACHPA-NHCH$_2$C(CH$_3$)$_3$
BOC-Phe-His-ACHPA-NHCH$_2$CH$_2$OH
BOC-Phe-His-ACHPA-Tau-OH
BOC-Phe-His-ACHPA-Tau-NH$_2$
BOC-Phe-His-ACHPA-$\beta$-Ala-OCH(CH$_3$)$_2$
BOC-Phe-His-ACHPA-NHCH$_2$CH$_2$NHCH(CH$_3$)$_2$
BOC-Phe-His-ACHPA-NHCH$_2$CH$_2$N(CH$_3$)Ph
[BOC-Phe-His-ACHPA-NHCH$_2$CH$_2$N(CH$_3$)$_2$CH$_2$Ph]$\oplus$Cl$^\ominus$
BOC-Phe-His-ACHPA-NHCH$_2$CH$_2$NHPh
BOC-Phe-His-ACHPA-cyclohexylamide
BOC-Phe-His-ACHPA-cycloheptylamide
BOC-Phe-His-ACHPA-NH(quinuclidin-4-yl)

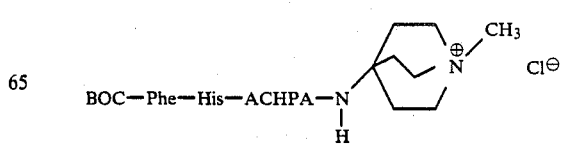

BOC-Phe-His-ACHPA-NH(quinuclidin-3-yl)

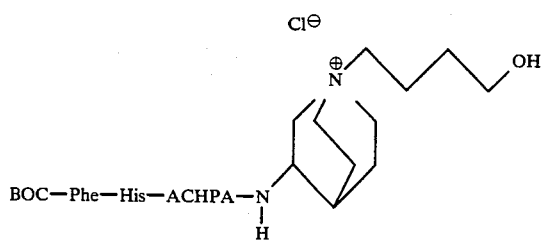

[BOC-Phe-His-ACHPA-NH(1,1-dimethylpiperidin-3-yl)]⊕Cl⊖
[IPOC-Phe-His-ACHPA-NH(1,1-dimethylpiperidin-3-yl)⊕Cl⊖
[IPOC-Phe-His-ACHPA-NH(1,1-dimethylpiperidin-4-yl)]⊕Cl⊖
BOC-Phe-[4-hydroxybutyl]Gly-ACHPA-NH-[(2S)-methyl]butyl
BOC-(p-OCH₃)Phe-His-ACHPA-NH-[(2S)-methyl]butyl
BOC-[3-(1-naphthyl)]Ala-His-ACHPA-NH-(2S)-methylbutyl
CBZ-3-(1-naphthyl)Ala-His-ACHPA-NH-(2S)-methylbutyl
[2-Phenylamino-3-phenylpropionyl]-His-ACHPA-NH-(2S)-methylbutyl
(N-Isopropyl)Val-Phe-His-ACHPA-NH-2(S)-methylbutyl
(N-Isopropyl)Gly-Phe-His-ACHPA-NH-2(S)-methylbutyl
(p-Diethylamino)benzyloxycarbonyl-Phe-His-ACHPA-NH-2(S)-methylbutyl
(p-Guanidino)benzyloxycarbonyl-Phe-His-ACHPA-NH-2(S)-methylbutyl
(p-Guanidinomethyl)benzyloxycarbonyl-Phe-His-ACHPA-NH-2(S)-methylbutyl
(p-Guanidinomethyl)benzoyl-Phe-His-ACHPA-NH-2(S)-methylbutyl
(p-Dimethylaminomethyl)benzoyl-Phe-His-ACHPA-NH-2(S)-methylbutyl
(p-Trimethylammonio)benzoyl-Phe-His-ACHPA-NH-2(S)-methylbutyl chloride hydrochloride
(p-Trimethylammonio)benzyloxycarbonyl-Phe-His-ACHPA-NH-2(S)-methylbutyl chloride hydrochloride
BOC-Phe-His-ACHPA-NH-CH(2-butyl)-CH₂-N(CH₂CH₂)₂O
BOC-Phe-His-ACHPA-NH-CH(2-butyl)-CH₂-N(CH₂CH₂)₂SO₂
[BOC-Phe-His-ACHPA-NH-CH(2-butyl)-CH₂-N(CH₃)(CH₂CH₂)₂O]⊕Cl⊖
BOC-Phe-His-ACHPA-NH-CH(2-butyl)-CH₂-N(CH₂CH₂)₂NCH₃
[BOC-Phe-His-ACHPA-NH-CH(2-butyl)-CH₂-N(CH₃)(CH₂CH₂)₂-NHCH₃]⊕Cl⊖
[BOC-Phe-His-ACHPA-NH-CH(2-butyl)-CH₂-N(CH₃)(CH₂CH₂)₂SO₂]⊕Cl⊖
[BOC-Phe-His-ACHPA-NH-CH(2-butyl)-CH₂-N(CH₂CH₂)₂N(CH₃)₂]⊕Cl⊖
BOC-Phe-His-ACHPA-NH-CH(2-butyl)-CH₂-N(CH₂CH₂)₂N-CO-CH₃
BOC-Phe-His-ACHPA-NH-CH(2-butyl)-CH₂-N(CH₃)₂
[BOC-Phe-His-ACHPA-NH-CH(2-butyl)-CH₂-N(CH₃)₃]⊕Cl⊖
[BOC-Phe-His-ACHPA-N(i-propyl)-CH(2-butyl)-CH₂-N(CH₃)₃]⊕Cl⊖
[BOC-Phe-His-ACHPA-N(CH₃)-CH(2-butyl)-CH₂-N(CH₃)₃]⊕Cl⊖
[BOC-Phe-His-ACHPA-N(i-butyl)-CH(2-butyl)-CH₂-N(CH₃)₃]⊕Cl⊖
[BOC-Phe-His-ACHPA-NH-CH(2-butyl)-CH₂-N(CH₂CH₃)₃]⊕Cl⊖
BOC-Phe-His-ACHPA-NH-CH(2-butyl)-CH₂-CH₂-N(CH₂CH₂)₂O
BOC-Phe-His-ACHPA-NH-CH(2-butyl)-CH₂-CH₂-N(CH₂CH₂)₂SO₂
[BOC-Phe-His-ACHPA-NH-CH(2-butyl)-CH₂-CH₂-N(CH₂CH₃)₃]⊕Cl⊖
[BOC-Phe-His-ACHPA-NH-CH(2-butyl)-CH₂-CH₂-CH₂-N(CH₂CH₃)₃]⊕Cl⊖
BOC-Phe-His-ACHPA-NH-CH(2-butyl)-CH₂-NH-(4,5-dihydroimidazol-2-yl)
BOC-Phe-His-ACHPA-NH-CH(2-butyl)-CH₂-NH-(1-ethyl-4,5-dihydroimidazol-2-yl)
[BOC-Phe-His-ACHPA-NH-CH(2-butyl)-CH₂-NH-(1-ethylpyridinium-4-yl
BOC-Phe-His-ACHPA-NH-CH(2-butyl)-CH₂-(3-aminopyrrolidin-1-yl)
[BOC-Phe-His-ACHPA-NH-CH(2-butyl)-CH₂-(1-methyl-3-oxopiperidinonium-1-yl)]⊕Cl⊖
BOC-Phe-His-ACHPA-NH-CH(2-butyl)-CH₂-(3-dimethylaminopiperidin-1-yl)
BOC-Phe-His-ACHPA-NH-CH(2-butyl)-CH₂-(3-trimethylammoniopiperidin-1-yl)
[BOC-Phe-His-ACHPA-NH-CH(2-butyl)-CH₂-NH-(1,1-dimethylpiperidinium-4-yl)]⊕Cl⊖
BOC-Phe-His-ACHPA-NH-CH(2-butyl)-CH₂-NH-(3,4,5,6-tetrahydropyrazol-2-yl)
BOC-Phe-His-ACHPA-NH-CH(2-butyl)-CH₂-NH-(1-methylazepin-3-yl)
[BOC-Phe-His-ACHPA-NH-CH(2-butyl)-CH₂-NH-(1,1-dimethylazepinonium-3-yl)]⊕Cl⊖
BOC-Phe-His-ACHPA-NH-CH(2-butyl)-CH₂-NH-(3-quinuclidinyl)
[BOC-Phe-His-ACHPA-NH-CH(2-butyl)-CH₂-NH-(N-methylquinuclidinonium-3-yl)]⊕Cl⊖
BOC-Phe-His-ACHPA-NH-CH(2-butyl)-CH₂-NH-CH₂Ph
BOC-Phe-His-ACHPA-NH-CH(2-butyl)-CH₂-N(CH₃)-CH₂Ph
[BOC-Phe-His-ACHPA-NH-CH(2-butyl)-CH₂-N(CH₃)-CH₂Ph]⊕Cl⊖
BOC-Phe-His-ACHPA-NH-CH(2-butyl)-CH₂-NH-CH₂-(4-pyridyl)
[BOC-Phe-His-ACHPA-NH-CH(2-butyl)-CH₂-NH-CH₂-(1-methylpyridinium-4-yl)]⊕Cl⊖
BOC-Phe-His-ACHPA-NH-CH(2-butyl)-CH₂-NH-CH₂-(1-ethylpyrrolidin-3-yl)
BOC-Phe-His-ACHPA-NH-CH(2-butyl)-CH₂-NH-CH₂-CH₂-N(CH₂CH₂)₂O
[BOC-Phe-His-ACHPA-NH-CH(2-butyl)-CH₂-NH-CH₂-CH₂N(CH₃)(CH₂CH₂)₂O]⊕Cl⊖
[BOC-Phe-His-ACHPA-NH-CH(i-butyl)-CH₂-N(CH₂CH₂)₂N(CH₃)₂]⊕Cl⊖
BOC-Phe-His-ACHPA-NH-CH(i-butyl)-CH₂-NH(1-ethyl-4,5-dihydroimidazol-2-yl)
BOC-Phe-His-ACHPA-NH-CH₂-CH(2-butyl)-N(CH₃)₂
[BOC-Phe-His-ACHPA-NH-CH₂-CH(2-butyl)-N(CH₂CH₃)₃]⊕OAc⊖
BOC-Phe-His-ACHPA-NH-CH₂-CH(2-butyl)-NH-(4,5-dihydroimidazol-2-yl)
BOC-Phe-His-ACHPA-NH-CH₂-CH(2-butyl)-NH-(1-ethyl-4,5-dihydroimidazol-2-yl)
BOC-Phe-His-ACHPA-NH-CH(2-butyl)-CH₂-(2-hydroxymethylpyrrolidin-1-yl)

BOC-Phe-His-ACHPA-NH-CH(2-butyl)-CH₂-(2-guanidinomethylpyrrolidin-1-yl)
[BOC-Phe-His-ACHPA-NH-CH(2-butyl)-CH₂-(2-hydroxymethyl-1-methylpyrrolidinium-1-yl)]⊕Cl⊖
BOC-Phe-His-ACHPA-NH-CH(2-butyl)-CH₂-(2-carboxy-1-methylpyrrolidinium-1-yl) inner salt
[BOC-Phe-His-ACHPA-NH-CH(2-butyl)-CH₂-(2-trimethylammoniomethylpyrrolidin-1-yl)]⊕Cl⊖
[BOC-Phe-His-ACHPA-NH-CH(2-butyl)-CH₂-N(CH₃)₂]⊖$^{CH_2CO_2}$⊖
[BOC-Phe-His-ACHPA-NH-CH(2-butyl)-CH(OH)-CH₂-N(CH₃)(CH₂CH₂)₂O]⊕AOc⊖
[BOC-Phe-His-ACHPA-NH-CH(2-butyl)-CH₂-(pyridinium-1-yl)]⊕Cl⊖
[BOC-Phe-His-ACHPA-NH-CH(2-butyl)-CH₂-1-methylimidazolium-yl)]⊕Cl⊖
BOC-Phe-His-ACHPA-NH-CH(2-butyl)-CH₂-N(CH₃)₂⊕CH₂CH₂CO₂⊖
BOC-Phe-His-ACHPA-NH-CH(2-butyl)-CH₂-N(CH₃)₂⊕CH₂CH₂SO₃⊖
[BOC-Phe-His-ACHPA-NH-CH(2-butyl)-CH₂-N(CH₃)₂CH₂CH₂OH]⊕Cl⊖
[BOC-Phe-His-ACHPA-NH-CH(2-butyl)-CH₂-N(CH₃)₂CH₂CH₂CH₂OH]⊕OAc⊕
[BOC-Phe-His-ACHPA-NH-CH(2-butyl)-CH₂-N(CH₃)₂CH₂CH₂N(CH₃)₂]⊕OAc⊕
[BOC-Phe-His-ACHPA-NH-CH(2-butyl)-CH₂-NH-CH₂CH₂N(CH₃)₃]⊕Cl⊖
BOC-Phe-His-ACHPA-NH-CH(2-butyl)-CH₂-NH-CH₂CH₂NH-C(=NH)NH₂
BOC-Phe-His-ACHPA-NH-CH(2-butyl)-CH₂-NH-CH₂CH(NH₂)CO₂H
BOC-Phe-His-ACHPA-NH-CH(2-butyl)-CH₂-NH-CH₂CH(CO₂)⊖N(CH₃)₃⊕
BOC-Phe-His-ACHPA-N(i-butyl)-CH₂-CH₂-N(CH₂CH₂)₂O
[BOC-Phe-His-ACHPA-N(i-butyl)-CH₂-CH₂-N(CH₃)(CH₂CH₂)₂O]⊕Cl⊖
[BOC-Phe-His-ACHPA-N(i-butyl)-CH₂-CH₂-N(CH₂CH₂)₂N(CH₃)₂]⊖Cl⊕
[BOC-Phe-His-ACHPA-N(i-butyl)-CH₂-CH₂-N(CH₃)₃]⊕Cl⊖
BOC-Phe-His-ACHPA-N(i-butyl)-CH₂-CH₂-N(CH₃)₂⊕CH₂CO₂⊖
BOC-Phe-His-ACHPA-NH-CH₂-CH(2-butyl)-N(O)(CH₃)₂
BOC-Phe-His-ACHPA-NH-CH(2-butyl)-CH₂-NH-CH₂(pyridin-4-yl-N-oxide)
BOC-Phe-His-ACHPA-NH-CH(2-butyl)-CH₂-NH-CH₂(pyridin-2-yl-N-oxide)
BOC-Phe-His-ACHPA-NH-CH(2-butyl)-CH₂-N(O)(CH₂CH₂)₂O
BOC-Phe-His-ACHPA-NH-CH(2-butyl)-CH₂-N(O)(CH₃)-CH₂Ph
BOC-Phe-His-ACHPA-NH-CH(2-butyl)-CH₂-NH-CH₂CH₂N(O)(CH₃)₂
BOC-Phe-His-ACHPA-NH-CH(2-butyl)-CH₂-NH-CH₂CH(CO₂H)N(O)(CH₃)₂
BOC-Phe-His-Cal[CH(OH)CH₂]Val-NH-(2(S)-methylbutyl)
BOC-Phe-His-Cal[CH(OH)CH₂]Val-NH-CH₂CH₂N(CH₂CH₂)₂O
BOC-Phe-His-Cal[CH(OH)CH₂]Val-NH-CH₂CH₂CH₂N(Ch₃)⊕(CH₂CH₂)₂OCl⊖
BOC-Phe-His-Cal[CH(OH)CH₂]Val-NH-CH₂CH₂N(CH₂CH₂)₂N(CH₃)₂⊕Cl⊖
BOC-Phe-His-Cal[CH(OH)CH₂]Val-NH-CH(2-butyl)-CH₂-N(CH₃)₂
BOC-Phe-His-Cal[CH(OH)CH₂]Val-NH-CH(2-butyl)-CH₂-N(CH₃)₃⊕Cl⊖
BOC-Phe-His-Cal[CH(OH)CH₂]Val-NH-CH₂(1-methylpyridinium-4-yl)]⊕Cl⊖

BOC-Phe-His-Cal[CH(OH)CH₂]Val-NH-CH(2-butyl)-CH₂-NH-(1-ethyl-4,5-dihydroimidazol-2-yl)
[BOC-Phe-His-Cal[CH(OH)CH₂]Val-NH-CH₂(1-methylpyridinium-2-yl)]⊕Cl⊖
[BOC-Phe-His-Cal[CH(OH)CH₂]Val-NH-CH₂ (4-trimethylammoniophenyl)]⊕Cl⊖
BOC-Phe-His-Cal[CH(OH)CH₂]Val-NH-(4-guanidinophenyl)
N-(4-dimethylaminophenyl)Phe-His-Cal[CH(OH)CH₂]Val-NHCH₂CH(CH₃)₂
[N-(4-trimethylammoniophenyl)Phe-His-Cal[CH(OH)CH₂]Val-NH-(2(S)-methylbutyl)]⊕Cl⊖
N-(3,4-dihydroxyphenyl)Phe-His-Cal[CH(OH)CH₂]-Val-NHCH₂CH(CH₃)₂
[Dibenzylacetyl-His-Cal[CH(OH)CH₂]Val-NH-CH₂CH₂N(CH₂CH₂)₂N(CH₃)₂]⊕Cl⊖
(N-t-butyl)Phe-His-Cal[CH(OH)CH₂]Val-NH-CH₂CH₂N(CH₂CH₂)₂O
(N-i-propyl)Phe-His-Cal[CH(OH)CH₂]Val-NH-CH₂CH₂N(CH₂CH₂)₂N(CH₃)
BOC-(3-dimethylamino)Phe-His-ACHPA-(2(S)-methylbutyl)
BOC-(o-isopropoxy)Phe-His-ACHPA-(2(S)-methylbutyl)
BOC-(p-isopropoxy)Phe-His-ACHPA-(2(S)-methylbutyl)
BOC-(m-aminomethyl-p-methoxy)Phe-His-ACHPA-(2(S)-methylbutyl) and
[BOC-[p-(N-methyl-N-trimethylammonioethyl)]Phe-His-ACHPA-(2(S)-methylbutyl)]⊕Cl⊖

More preferred compounds include Boc-Phe-His-ACHPA-NH-[1-(4-hydroxylbutyl)-quinuclidinium-3-yl]acetate; Boc-Phe-His-ACHPA-NH-[1-(2-pyridylmethyl)-quinuclidinium-3-yl]acetate; Boc-Phe-His-ACHPA-NH-(1-methylquinuclidinyl-3-yl) acetate; [Boc-Phe-His-ACHPA-NH-CH(2-butyl)-CH₂-N(CH₃)(CH₂-N(CH₃)(CH₂CH₂)₂O]⊕OAc⊖; [Boc-Phe-His-ACHPA-NH-CH(2-butyl)-CH₂N(CH₃)(CH₂CH₂)₂ NCH₃]⊕Cl⊖; [Boc-Phe-His-ACHPA-NH-CH(2-butyl)-CH₂-NH(CH₂CH₂)₂N(CH₃)₂ ⊕OAc⊕; Boc-Phe-His-ACHPA-NH-CH(2-butyl)-CH₂-N(CH₃)₃⊕OAc⊖; [Boc-Phe-His-ACHPA-NH-CH(2-butyl)-CH₂-NH-(1,1-dimethylazepinonnium-3-yl)]⊕Cl⊖; and [Boc-Phe-His-ACHPA-NH-CH(2-butyl)-CH₂-N(CH₃)₂-CH₂Ph]⊕OAc⊖.

The pharmaceutically-acceptable salts of the peptides of Formula I (in the form of water- or oil-soluble or dispersible products) include the conventional non-toxic salts or the quaternary ammonium salts of these peptides, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Peptide renin inhibitors of Formula I may be prepared in accordance with well-known procedures for preparing peptides from their constituent amino acids.

Structures and abbreviations for the G components of the renin-inhibitory peptides of the present invention include:

1.
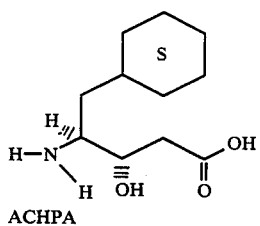
ACHPA with BOC-ACHPA-OEt being prepared by the method described by Boger et al, *J. Med. Chem* 1985, 28, 1779–1790;

2.
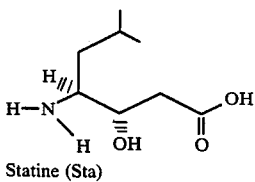
Statine (Sta)

with BOC-Sta-OEt being prepared in accordance with the procedure described by Rich et al, *J. Org. Chem.*, 43, 3624(1978);

3.
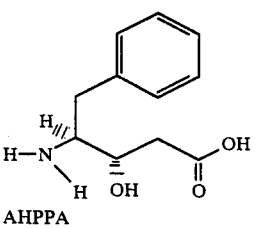
AHPPA with BOC-AHPPA-OEt being prepared as described by Rich et al, *J. Med. Chem.*, 23, 27–33 (1980);

4.
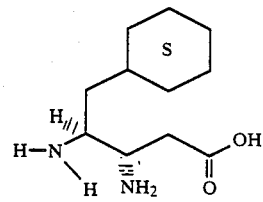
AmACHPA

5.
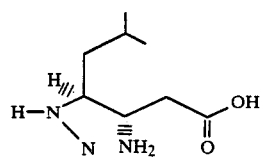
AmSta with BOC-AmSta(CBZ)-OH being prepared as shown in the following scheme, and BOC-AmACHPA(CBZ)-OH being prepared as illustrated in the scheme by substituting BOC-ACHPA-OEt for BOC-Sta-OEt:

Synthesis of protected 3-amino-3-deoxy-(3S, 4S)-Statine:

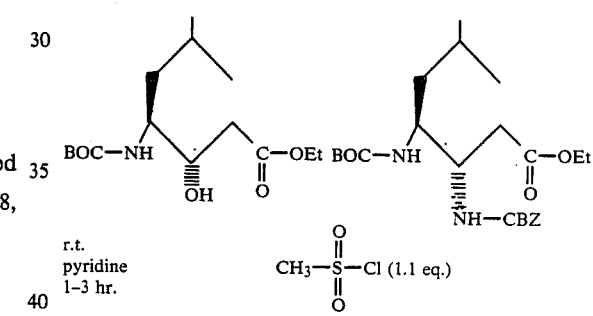

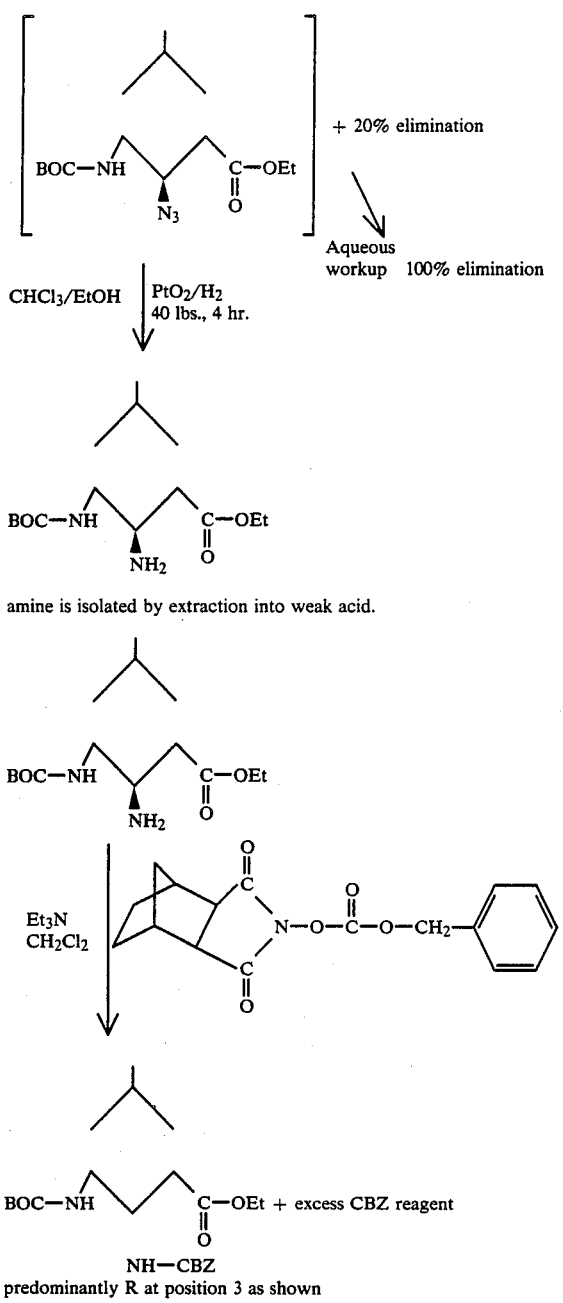

Base hydrolysis gives the free acid or incorporation into the synthesis of the peptides of Formula I; or alternatively, this material may be prepared as described by Jones et al, in *Peptides, Structure and Function. Proceedings of the Ninth American Peptide Symposium* (eds. C. M. Deber, V. J. Hruby and K. D. Kopple) pp. 759–62, 1985, Pierce Chemical Co., Rockford, Ill.; Arrowsmith et al, *J. Chem. Soc. Chem. Commun.* 755–7 (1986); and Raddatz et al, Published Eur. Pat. Appl. No. 161,588; with efficient methods for preparing the 2-substituted statine component G (such as

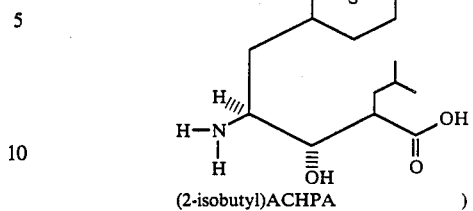

(2-isobutyl)ACHPA in a suitably protected form being described in Pub. Eur. Pat Appln. No. 157,409 (with other pertinent references including D. Veber et al, *Biochem. Soc. Trans.*, 12, 956–959 (1984) and H. Stein et al. *Fed. Proc.* 45, 869, Abstract No. 4151 (1986); and

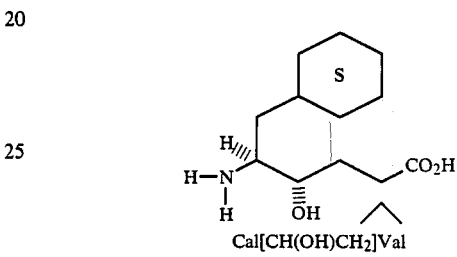

Cal[CH(OH)CH$_2$]Val with BOC-Cal[CH(OH)CH$_2$]Val-OH lactone being obtained from intermediates prepared using methods described by P. Buhlmayer et al, in Published European Patent Application No. 184,550-A2, and synthetic routes to similar peptide bond isosteres being described in the following:

a. Szelke et al, in *Peptides, Structure and Function. Proceedings of the Eighth American Peptide Symposium* (ed. V. J. Hruby and D. H. Rich) pp. 579–82, Pierce Chemical Co., Rockford, Ill.;
b. D. T. Pals et al in European Patent Appln. No. 173,481-A2;
c. B. E. Evans et al, *J. Org. Chem.*, 50, 4615–1625 (1985);
d. A. H. Fray et al, *J. Org. Chem.*, 51, 4828–4833 (1986);
e. M. Szelke et al, PCT Int. Appl. WO No.84 03,044; and
f. D. J. Kempf, *J. Org Chem.*, 51, 3921–3926 (1986).

Peptides of Formula I which contain ACHPA as a peptide bond mimic are prepared using the following procedures:

(As used in these routes, $R^{2a}$ and $R^{2b}$ are as defined above, and the amine components, $R^{2c}R^{2d}NH$, are intended to represent all those encompassed by the definition of J, including primary and secondary amines.)

Route A

Step A1: BOC-ACHPA-OEt is treated with anhydrous TFA to remove the BOC protecting group, giving ACHPA-OEt;

Step A2: Using standard methods, a dipeptide protected at the N-terminus with a BOC group (BOC-AA$^2$-AA$^1$) is coupled to ACHPA-OEt, giving a coupled product 3 or alternatively, BOC-AA$^1$ is coupled to ACHPA-OEt to give product 1. The coupled product 1 is then treated with anhydrous TFA to remove the Boc protecting group, and the resulting product 2 is coupled with BOC-AA$^2$, to give 3;

Step A3: The resulting coupled product 3 is treated with methanolic hydrazine, giving the corresponding hydrazide 4;

Step A4: Hydrazide 4 is treated with acidic isoamyl nitrite, producing the corresponding acyl azide, which is treated in situ with an amine $R^{2c}R^{2d}NH$, giving coupled product 5, or alternatively, coupled product 3 is treated with sodium hydroxide in THF-H$_2$O and the resulting carboxylic acid derivative coupled with Rhu 2cR$^{2d}$NH, to give 5. Additional reactive functional groups in the amino component $R^{2c}R^{2d}NH$ are protected with protecting groups, such as CBZ for amino groups, benzyl ether for alcohols, and benzyl esters for carboxylic acids;

Step A5: The N-terminal BOC protecting group is then removed from 5 by treatment with anhydrous TFA, and the resulting tripeptide analog 6 treated with an acylating agent represented by $R^{2a}(R^{2b})X$-CO-W, where this acylating agent is an acid chloride or other activated carboxylic acid derivative, to give acylated tripeptide derivative 7.

Step A5a: Alternatively, compound 7 may be prepared by coupling an acylated amino acid $R^{2a}(R^{2b})X$-CO-AA$^2$ to compound 2, which is prepared as described in steps A1 and A2, and treating the resulting coupled product 3a as described for compound 3 in steps 2 and 3, to first give hydrazide 4a, then, after coupling to $R^{2c}R^{2d}NH$, to give the coupled product 7;

Step A6: During the steps above, reactive functional groups present in the side-chains of amino acid components or in the $R^{2c}R^{2d}NH$- element are protected with protecting groups, such as CBZ groups for amines, benzyl ethers for alcohols, and benzyl esters for carboxylic acids, or in the case of histidine, the BOC protecting may be used for protection of the side-chain imidazole ring and removed in step A3, during the treatment with hydrazine, or in step A4, during treatment with sodium hydroxide, thereafter, leaving the histidine imidazole ring unprotected, or alternatively, DNP protection may be used on the sidechain imidazole ring;

Step A7: Protecting groups are removed from 7 by hydrogenolysis, or when the DNP group is used, by 10% thiophenol in DMF, giving compound 8;

Step A8: In cases where a quaternized amino group is to be introduced into the C-terminal $R^{2c}R^{2d}NH$- element of compound 8, one of the following procedures is followed to introduce the quaternized amine group:

Procedure 1: A tertiary amine within the $R^{2c}$ or $R^{2d}$ group of $R^{2c}R^{2d}NH$ is quaternized by treatment of $R^{2c}R^{2d}NH$-BOC with an alkyl halide and KHCO$_3$ in methanol or ethanol, or with an alkyl halide in DMF, and the resulting quaternary ammonium salt is treated with anhydrous TFA to remove the BOC protecting group, with the resulting amine used in coupling step 3 above.

Procedure 2: A compound 7, in which the $R^{2c}R^{2d}N$-element contains a tertiary amine, is prepared according to steps A1 to A6, and then the tertiary amine, is quaternized by treatment with an alkyl halide in DMF, wherein histidine, when present as the AA$^1$ element, must first be reprotected as the BOC derivative by treatment of 7 with di-t-butyldicarbonate, with the BOC group being removed after step A7 by treatment of compound 8 with K$_2$CO$_3$ in methanol or with anhydrous ammonia in DMF or methanol; and Step A9: In cases where the $R^{2c}R^{2d}N$-component of a compound 8 contains a guanidine group, compound 7 is prepared as described in steps A1, A2 A3 and A5a above, with an amine group, present in the $R^{2c}R^{2d}N$-component and heretofore protected with a BOC group, being liberated by treatment of 7 with anhydrous TFA, and the quanidine group being introduced using standard methods, removing other protecting groups as described in step A7.

| | Compound Formula |
|---|---|
| 1 | BOC—AA$^1$—ACHPA—OEt |
| 2 | AA$^1$—ACHPA—OEt |
| 3 | BOC—AA$^2$—AA$^1$—ACHPA—OEt |
| 3a | $R^{2a}(R^{2b})$X—CO—AA$^2$—AA$^1$—ACHPA—OEt |
| 4 | BOC—AA$^2$—AA$^1$—ACHPA—NHNH$_2$ |
| 4a | $R^{2a}(R^{2b})$X—CO—AA$^2$—AA$^1$—ACHPA—NHNH$_2$ |
| 5 | BOC—AA$^2$—AA$^1$—ACHPA—NR$^{2c}$R$^{2d}$ |
| 6 | AA$^2$—AA$^1$—ACHPA—NR$^{2c}$R$^{2d}$ |
| 7,8 | $R^{2a}(R^{2b})$X—CO—AA$^2$—AA$^1$—ACHPA—NR$^{2c}$R$^{2d}$ |

Route B

Step B1: BOC-ACHPA-OEt is treated with sodium hydroxide in THF-H$_2$O, to give BOC-ACHPA;

Step B2: BOC-ACHPA-OH is coupled with an amine component $R^{2c}R^{2d}NH$, to give coupled product 9;

Step B3: Compound 9 is treated with anhydrous TFA to remove the BOC protecting group, to give compound 10;

Step B4: Compound 10 is coupled with a dipeptide protected at the N-terminus with a BOC protecting group (BOC-AA$^2$-AA$^1$), to give coupled product 12, or alternatively, 10 is coupled with BOC-AA$^1$, to give compound 11, which is treated with anhydrous TFA and the resulting product is coupled with BOC-AA$^2$ to give compound 12;

Step B5: The N-terminal BOC protecting group is then removed from compound 12 by treatment with anhydrous TFA, and the resulting tripeptide analog 13 is treated with an acylating agent, represented by $R^{2a}(R^{2b})$X-CO-W, where this acylating agent is an acid chloride or other activated carboxylic acid derivative, to give acylated tripeptide derivative 7;

Step B6: The protecting groups, which, as described in Route A, have been used to protect reactive functional groups in amino acid side chains of AA$^1$ and AA$^2$ and in the $R^{2c}R^{2d}N$- component during the coupling steps above, are removed from coupled Product 7 by hydrogenolysis and hydrolysis to give compound 8; and Step B7: In cases where a quaternized amino group is to be introduced into the C-terminal $R^{2c}R^{2d}N$- element of compound 8, one of the following procedures is followed to introduce the quaternized amine group:

Procedure 1: A tertiary amine within the $R^{2c}$ or $R^{2d}$ group of $R^{2c}R^{2d}NH$ is quaternized by treatment of $R^{2c}R^{2d}N$-BOC with an alkyl halide and KHCO$_3$ in methanol or ethanol, or with an alkyl halide in DMF, and the resulting quaternary ammonium salt is treated with anhydrous TFA to remove the BOC protecting group, which results in an amine used in coupling step 3 above;

Procedure 2: A compound 7, in which the $R^{2c}R^{2d}N$-element contains a tertiary amine, is prepared according to steps B1 to B5, and the tertiary amine is quaternized by treatment with an alkyl halide in DMF, or when histidine is present as the AA$^2$ element, it must first be reprotected as the BOC derivative by treatment of 7 with di-t-butyldicarbonate, with the BOC group being removed after step A7 by treatment of compound 8 with $K_2CO_3$ in methanol or with anhydrous ammonia in DMF or methanol.

| Compound | Formula |
|---|---|
| 9 | BOC—ACHPA—$NR^{2c}R^{2d}$ |
| 10 | ACHPA—$NR^{2c}R^{2d}$ |
| 11 | BOC—$AA^1$—ACHPA—$NR^{2c}R^{2d}$ |
| 12 | BOC—$AA^2$—$AA^1$—ACHPA—$NR^{2c}R^{2d}$ |
| 13 | $AA^2$—$AA^1$—ACHPA—$NR^{2c}R^{2d}$ |

Peptides of Formula I which contain ACHPA as a PePtide bond mimic, and which have more than two amino acids coupled to the amino terminus of ACHPA, may be prepared using the procedures described in Route A. In this case, compound 6 (prepared as described in steps A1 through A5), is coupled to additional BOC-protected amino acids (BOC-$AA^3$, BOC-$AA^4$, etc) using standard coupling methods. After each coupling step, the amino-terminal BOC-protecting group is removed from the coupling product by treatment with anhydrous TFA, until after the final coupling and TFA-treatment, the resulting product is treated as described in route A above for compound 6.

Peptides of Formula I which contain statine are prepared as described above in routes A and B, except that BOC-ACHPA-OEt, is replaced with BOC-Sta-OEt, resulting in peptides such as 14.

| 14 | 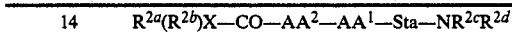 |

Peptides of Formula I which contain amino-ACHPA (AmACHPA) or amino-statine (AmSta) are prepared as described above in Routes A and B, except that BOC-ACHPA-OEt is replaced with BOC-AmACHPA(CBZ)-OEt or with BOC-AmSta(CBZ)-OEt, with the CBZ group of the AmACHPA or AmSta element being removed by hydrogenolysis in step A7 or B6. In this way, peptide such as 15 (and the corresponding AmSta analog) may be prepared.

| 15 | $R^{2a}(R^{2b})X$—CO—$AA^2$—$AA^1$—AmACHPA—$NR^{2c}R^{2d}$ |

Peptides of Formula I which contain a 2-substituted statine or ACHPA element as a peptide bond mimic may be prepared as described above in Routes A and B, except that BOC-ACHPA-OEt is replaced with a suitably protected 2-substituted ACHPA or 2-substituted statine derivative, for example BOC-(2-allyl)ACHPA-OEt or BOC-(2-isobutyl)Sta-OEt, resulting in peptides such as 16, 17, and 18.

| 16 | $R^{2a}(R^{2b})X$—CO—$AA^2$—$AA^1$—(2-isobutyl)ACHPA—$NR^{2c}R^{2d}$ |
| 17 | $R^{2a}(R^{2b})X$—CO—$AA^2$—$AA^1$—(2-allyl)ACHPA—$NR^{2c}R^{2d}$ |
| 18 | $R^{2a}(R^{2b})X$—CO—$AA^2$—$AA^1$—(2-isoamyl)Sta—$NR^{2c}R^{2d}$ |

Peptides of Formula I which contain Cal[CH(OH)$CH_2$]Val as a peptide bond mimic are prepared as described in Routes C and D:

Route C

Step C1: The Boc protecting group is removed from lactone 19 by treatment with anhydrous TFA, to give lactone 19a;

Step C2: Lactone 19a is coupled with a Boc-protected amino acid (Boc-$AA^1$) to give 20a, or with an N-terminal Boc-protected dipeptide (Boc-$AA^2$-$AA^1$) to give 20b, or compound 20b may be prepared by treating 20a with anhydrous TFA, and coupling the product with Boc-$AA^2$. Treatment of 20a (or 20b) with anhydrous TFA and coupling of the product with $R^{2a}(R^{2b})X$-CO-W yields 21a (or 21b);

| 19 | BOC—Cal[CH(OH)$CH_2$]Val lactone |
| 19a | Cal[CH(OH)$CH_2$]Val lactone |
| 20a | BOC—$AA^1$—Cal[CH(OH)$CH_2$]Val lactone |
| 20b | BOC—$AA^2$—$AA^1$—Cal[CH(OH)$CH_2$]Val lactone |
| 21a | $R^{2a}(R^{2b})X$—CO—$AA^2$—$AA^1$—Cal[CH(OH)$CH_2$]Val lactone |
| 21b | $R^{2a}(R^{2b})X$—CO—$AA^1$—Cal[CH(OH)$CH_2$]Val lactone |

Step C3: Lactone 21a (or 21b) is then treated with aqueous potassium hydroxide to give the corresponding hydroxyacid, which is treated with t-butyldimethylsilyl chloride and imidazole, then with HOAc in THF-$H_2O$, to give the protected hydroxyacid 22a (22b);

| 22a | $R^{2a}(R^{2b})X$—CO—$AA^2$—$AA^1$—Cal[CH(OTBDMS)$CH_2$]Val—OH |
| 22b | $R^{2a}(R^{2b})X$—CO—$AA^1$—Cal[CH(OTBDMS)$CH_2$]Val—OH |

Step C4: Compound 22a (22b) is coupled with an amino component $R^{2c}R^{2d}NH$, to give 23a (23b), with additional reactive functional groups in the amino component $R^{2c}R^{2d}NH$ being protected with groups such as CBZ for amino and guanidino groups, benzyl ethers for alcohols, and benzyl esters for carboxylic acids;

| 23a | $R^{2a}(R^{2b})X$—CO—$AA^2$—$AA^1$—Cal[CH(OTBDMS)$CH_2$]Val—$NR^{2c}R^{2d}$ |
| 23b | $R^{2a}(R^{2b})X$—CO—$AA^1$—Cal[CH(OTBDMS)$CH_2$]Val—$NR^{2c}R^{2d}$ |

Step C5: The silyl protecting group is removed from 23a (23b) by treatment with tetrabutylammonium fluoride in THF-DMF, and other protecting groups are removed by hydrogenolysis, to give 24a (24b);

| 24a | $R^{2a}(R^{2b})X$—CO—$AA^2$—$AA^1$—Cal[CH(OH)$CH_2$]Val—$NR^{2c}R^{2d}$ |
| 24b | $R^{2a}(R^{2b})X$—CO—$AA^1$—Cal[CH(OH)$CH_2$]Val—$NR^{2c}R^{2d}$ |

Step C6: It is understood that during the steps above, the reactive functional groups in the side-chains of the amino acids $AA^1$ and $AA^2$ are protected with protecting groups, such as CBZ for amines and guanidines, and benzyl ethers for alcohols, which are removed during the hydrogenolysis of step C5, or when histidine is used as an amino acid component, the side-chain imidazole ring may be protected during step C2 with a BOC protecting group, which is removed during treatment with TFA, and the imidazole ring is left unprotected during subsequent N-terminal coupling or acylation reactions, or alternatively, histidine may be protected with a DNP protecting group during step C2, and this DNP group is removed in step C3 during the potassium hydroxide treatment; and Step C7: In some cases, a quaternized amino group is present in the C-terminal $R^{2c}R^{2d}N$- element of compound 24a (24b), and when it is, a tertiary amine within $R^{2c}$ or $R^{2d}$ of $R^{2c}R^{2d}NH$ is quaternized by treatment of $R^{2c}R^{2d}$N-BOC with an alkyl halide and KHCO$_3$ in methanol or ethanol or with an alkyl halide in DMF, with the resulting quaternary ammonium salt being treated with anhydrous TFA to remove the BOC protecting group, resulting in an amine used in coupling step C2 above.

Alternatively, a compound 23a (23b) containing a tertiary amine in the $R^{2c}R^{2d}$N-element may be prepared as described above in steps C1 to C6, with the silyl protecting group being removed from 23a (23b) by treatment with fluoride. If histidine is present as the AA$^1$ component, the imidazole ring is then protected by treatment with di-t-butyldicarbonate and Et$_3$N in methanol or DMF, and the tertiary amine present in the $R^{2c}R^{2d}$N-element is then quaternized by treatment with an alkyl halide in DMF. Protecting groups present in the molecule are then removed by hydrogenolysis, to give 24a (24b), with the BOC protecting group being removed from the histidine group, when present as the AA$^1$ component, by treatment of 24a (24b) with potassium carbonate in methanol, or with anhydrous ammonia in either methanol or DMF.

Route D

Step D1: Lactone 19 is treated with potassium hydroxide to give the corresponding hydroxyacid 25, which is treated with t-butyldimethylsilyl chloride and imidazole, then with HOAc in THF-H$_2$O, to give the protected hydroxyacid 26;

| | |
|---|---|
| 25 | BOC—Cal[CH(OH)CH$_2$]Val—OH |
| 26 | BOC—Cal[CH(OTBDMS)CH$_2$]Val—OH |

Step D2: Protected hydroxyacid 26 is coupled with an amino component $R^{2c}R^{2d}$NH, to give 27, with additional reactive functional groups in the amino component $R^{2c}R^{2d}$NH being protected with groups such as CBZ for amino and guanidino groups, benzyl ethers for alcohols, and benzyl esters for carboxylic acids;

Step D3: The BOC protecting group is removed from 27 by treatment with anhydrous TFA, to give compound 28;

| | |
|---|---|
| 27 | BOC—Cal[CH(OTBDMS)CH$_2$]Val—NR$^{2c}$R$^{2d}$ |
| 28 | Cal[CH(OTBDMS)CH$_2$]Val—NR$^{2c}$R$^{2d}$ |

Step D4: Compound 28 is coupled with a BOC-protected amino acid (BOC-AA$^1$) or a dipeptide with an N-terminal BOC protecting group (BOC-AA$^2$-AA$^1$), to give coupled product 29a (29b);

| | |
|---|---|
| 29a | BOC—AA$^1$—Cal[CH(OTBDMS)CH$_2$]Val—NR$^{2c}$R$^{2d}$ |
| 29b | BOC—AA$^2$—AA$^1$—Cal[CH(OTBDMS)CH$_2$]Val—NR$^{2c}$R$^{2d}$ |

Step D5: The N-terminal BOC protecting group of 29a (29b) is removed by treatment with anhydrous TFA in CH$_2$Cl$_2$, to give 30a (30b);

| | |
|---|---|
| 30a | AA$^1$—Cal[CH(OTBDMS)CH$_2$]Val—NR$^{2c}$R$^{2d}$ |
| 30b | AA$^2$—AA$^1$—Cal[CH(OTBDMS)CH$_2$]Val—NR$^{2c}$R$^{2d}$ |

Step D6: Compound 30a (30b) is treated with an acylating agent represented by $R^{2a}(R^{2b})$X-CO-W, where this acylating agent is an acid chloride or other activated carboxylic acid derivative, to give acylated tripeptide derivative 31a (31b), with additional reactive functional groups in $R^{2a}(R^{2b})$X-CO-W being protected with protecting groups as described above;

| | |
|---|---|
| 3a | $R^{2a}(R^{2b})$X—CO—AA$^1$—Cal[CH(OTBDMS)CH$_2$]Val—NR$^{2c}$R$^{2d}$ |
| 31b | $R^{2a}(R^{2b})$X—CO—AA$^2$—AA$^1$—Cal[CH(OTBDMS)CH$_2$]Val—NR$^{2c}$R$^{2d}$ |

Step D7: The silyl protecting group is removed from 31a (31b) by treatment with fluoride, with other protecting groups being removed by hydrogenolysis, to give 24a (24b);

Step D8: In some cases a quaternized amino group is present in the C-terminal $R^{2c}R^{2d}$N- element of compound 24a (24b), with a tertiary amine within $R^{2c}$ or $R^{2d}$ of $R^{2c}R^{2d}$NH being quaternized by treatment of $R^{2c}R^{2d}$N-BOC with an alkyl halide and KHCO$_3$ in methanol or ethanol or with an alkyl halide in DMF, and the resulting quaternary ammonium salt is treated with anhydrous TFA to remove the BOC protecting group, resulting in an amine used in coupling step D2 above; or Alternatively, a compound 31a (31b) containing a tertiary amine in the $R^{2c}R^{2d}$N- element may be prepared as described above in steps D1 to D6, with the silyl protecting group being removed from 31a (31b) by treatment with fluoride, or if histidine is present as the AA$^1$ component, the imidazole ring is protected next by treatment with di-t-butyldicarbonate and Et$_3$N in methanol or DMF, and the tertiary amine present in the $R^{2c}R^{2d}$N- element is quaternized by treatment with an alkyl halide in DMF. Protecting groups present in the molecule are then removed by hydrogenolysis (and hydrolysis), as described in step D7, to give 24a (24b);

Step D9: It is understoood that during the steps above, the reactive functional groups in the side-chains of amino acid components are protected with protecting groups, such as CBZ for amines and guanidines, and benzyl ethers for alcohols, which are removed in the above hydrogenolysis step, or if histidine is present as AA$^1$, the side-chain imidazole ring is protected with a BOC group which is removed by TFA in step D5, and thereafter, the side-chain of histidine is left unprotected. Alternatively, histidine with a DNP protecting group may be used, and the DNP group is removed after step D7 by treatment of 33a (33b) with thiophenol in DMF. Where the component G is carbonyl-reduced ACHPA:

A. Ethers

These analogs are prepared starting with Boc-ACHPA-OEt, simultaneously protecting NH and OH as an acetonide, and reducing the ester of the protected derivative with diisobutylaluminum hydride (Dibal), with the resultant alcohol being converted to a mesylate. The mesylate is displaceable with a variety of alkoxides to form ACHPA-ether derivatives, which are converted to the final renin inhibitors by sequentially deblocking with acid, coupling via the azide method with Boc-Phe-His(DNP)-NHNH$_2$, and removal of the DNP group with thiophenol.

Synthesis of Ether Analogs

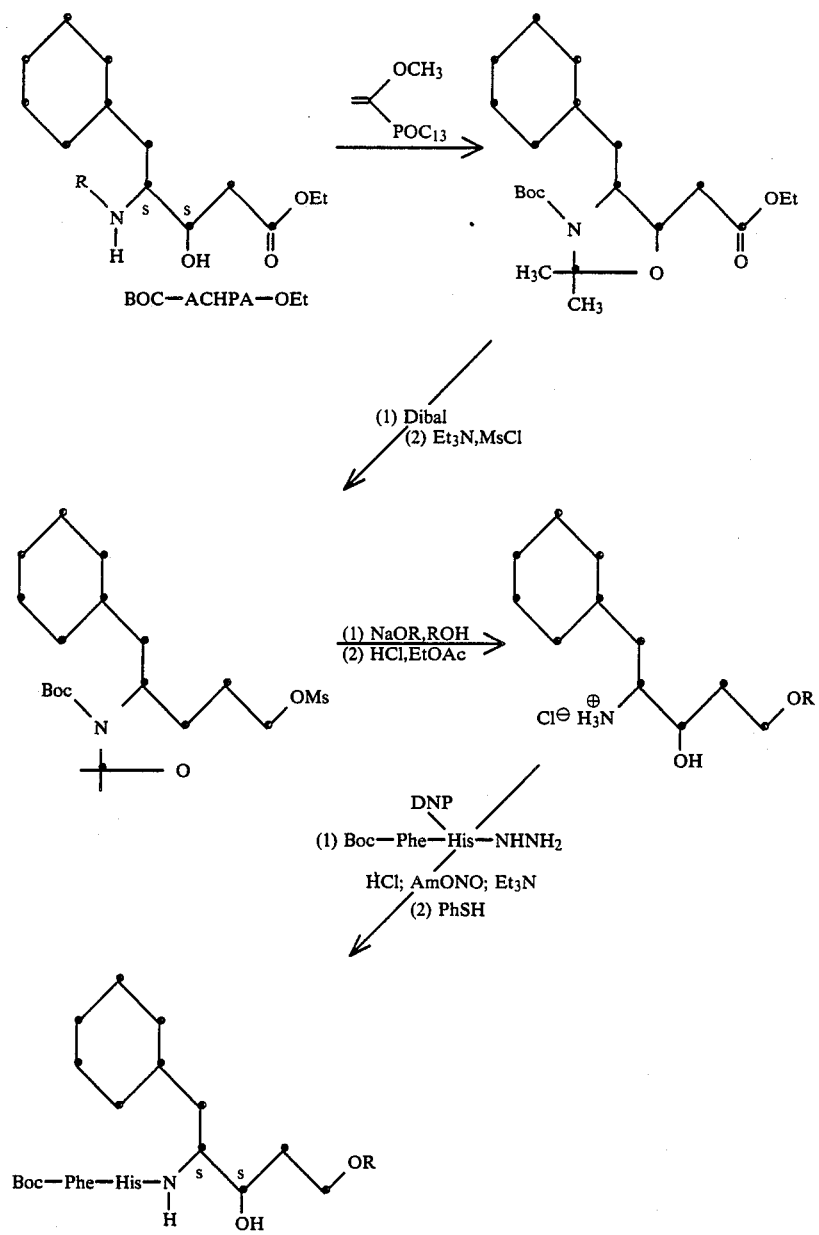

B. Amines

Boc-cyclohexylalanine methyl ester is reduced with Dibal to the aldehyde, which is then reacted with the lithium salt of acetonitrile. The 3S, 4S-diastereomer is separated from the mixtue and reduced with hydrogen over Raney nickel (Ra/Ni) to the amine. The amine is protected with Cbz and sequentially deblocked (-Boc) with TFA, coupled with Boc-(DNP)-His-OH via mixed anhydride, deblocked with TFA, coupled with Boc-Phe-OH, and deblocked (-DNP) with thiophenol. The Cbz group is removed catalytically and the resultant amine is alkylated to a variety of substituted amines with aldehydes in the presence of NaBH₃CN.

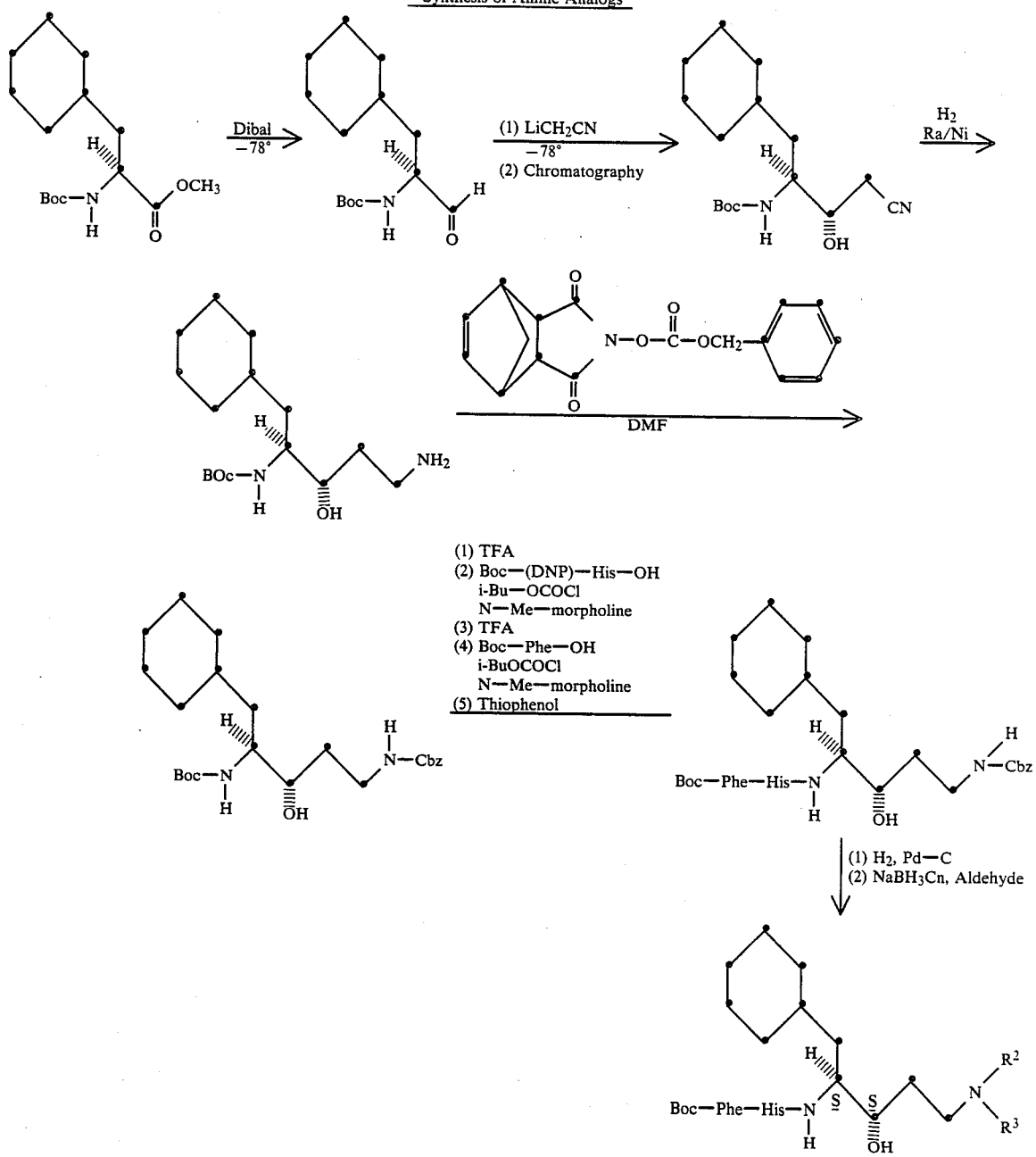

Synthesis of Amine Analogs

The novel inhibitory peptides of the present invention may also be prepared by using the solid phase sequential synthesis technique conducted in a stepwise manner on synthetic chloromethylated resin beads (20–70 microns in diameter) prepared by copolymerization of styrene with 1–2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino-protected derivative and the carboxyl group of the selected C-terminal amino acid is bound covalently to the insoluble polymeric resin support. For example, binding is effected as the carboxylic ester of the resin-bonded benzyl chloride present in chloromethyl-substituted polystyrene-divinylbenzene resin. The amino protecting group is then removed and the amino-protected derivative of the next amino acid in the sequence is added along with a coupling agent, such as dicyclohexylcarbodiimide, with the amino acid reactant employed in the form of a carboxyl-activated amino acid such as ONP ester, an amino acid azide, or the like. Deprotection and addition of successive amino acids is performed until the desired linear peptide is formed.

The selection of protecting groups is, in part, dictated by particular coupling conditions, in part by the amino acid and peptide components involved in the reaction.

Such amino-protecting groups ordinarily employed include those which are well known in the art, for example, urethane protecting substituents such as benzyloxycarbonyl (carbobenz-oxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid, in part because the BOC protecting group is readily removed following such coupling reaction and prior to the subsequent step by the relatively mild action of acids (i.e. trifluoroacetic acid, or hydrogen chloride in ethyl acetate).

The OH group of Thr and Ser may be protected by the Bzl group and the ε-amino group of Lys may be protected by the INOC group or the 2-chlorobenzyloxycarbonyl (2-Cl-CBZ) group. Neither group is affected by TFA, used for removing BOC protecting groups. After the peptide is formed, the protective groups such as 2-Cl-CBZ and Bzl, may be removed by treatment with HF or by catalytic hydrogenation.

After the peptide has been formed on the solid phase resin, it may be removed from the resin by a variety of methods which are well known in the art. For example, the peptide may be cleaved from the resin with hydrazine, by ammonia in methanol, or by methanol plus a suitable base.

The novel peptides of the present invention possess a high degree of activity in treating renin-associated hypertension, hyperaldosteronism and/or congestive heart failure in humans, as well as in other warm-blooded animals such as mice, rats, horses, dogs and cats.

For these purposes, the peptides of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating renin-associated hypertension, hyperaldosteronism, and/or congestive heart failure. This treatment involves administering to a patient in need of such treatment a pharmaceutical composition comprising a pharmaceutical carrier and a therapeutically-effective amount of a peptide of the formula:

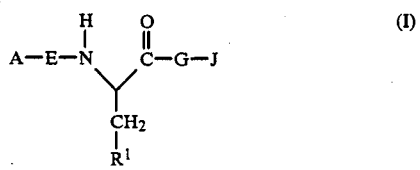

(I)

wherein A, E, $R^1$, G, and J are defined above, or a pharmaceutically-acceptable salt thereof.

These pharmaceutical compositions may be in the form of orally-administrable suspensions or tablets; nasal sprays; sterile injectable preparations, for example, as sterile injectable aqueous or oleagenous suspensions; or suppositories.

When administered orally as a suspension, these compositions may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared as solutions in saline, employing benzyl alcohol or other suitable preservatives, absorption promoters to enhance bioavailability, flourocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

Dosage levels of the order of 0.02 to 2.0 grams-per-day are useful in the treatment of the above-indicated conditions, with oral doses two-to-five times higher. For example, renin-associated hypertension and hyperaldosteronism are effectively treated by the administration of from 10 to 50 milligrams of the compound per kilogram of body weight from one to three times per day. It will be understood, however, that the specific dose level and frequency of dosage for any particular patient will depend upon a variety of factors including the activity of the specific compound employed, the metabolic stability and length of action of that compound, the age, body weight, general health, sex, diet, mode and time of administration, rate of excretion, drug combination the severity of the particular condition, and the host undergoing therapy.

The present invention is also directed to combinations of the novel renin-inhibitory peptides of Formula I with one or more antihypertensive agents selected from the group consisting of diuretics, α- and/or β-adrenergic blocking agents, CNS-acting agents, adrenergic neuron blocking agents, vasodilators, angiotensin I converting enzyme inhibitors, calcium channel blockers, and other antihypertensive agents.

For example, the compounds of this invention can be given in combination with such compounds or salt or other derivative forms thereof as:

Diuretics: acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate; sodium nitroprusside; spironolactone; ticrynafen; triamterene; trichlormethiazide;

α-Adrenergic Blocking Agents: dibenamine; phentolamine; phenoxybenzamine; prazosin; tolazoline;

β-Adrenergic Blocking Agents: atenolol; metoprolol; nadolol; propranolol; timolol;
((±)-2-[3-(tert-butylamino)-2-hydroxypropoxy]-2-furananilide) (ancarolol);
(2-acetyl-7-(2-hydroxy-3-isopropylaminopropoxy)benzofuran HCl) (befunolol);
((±)-1-(isopropylamino)-3-(p-(2-cyclopropylmethoxyethyl)-phenoxy)-2-propranol HCl) (betaxolol);
(1-[(3,4-dimethoxyphenethyl)amino]-3-(m-tolyloxy)-2-propanol HCl) (bevantolol);
((±)-1-(4-((2-isopropoxyethoxy)methyl)phenoxy)-3-isopropylamino-2-propanol)fumarate) (bisoprolol);
(4-(2-hydroxy-3-[4-(phenoxymethyl)-piperidino]-propoxy)-indole);
(carbazolyl-4-oxy-5,2-(2-methoxyphenoxy)-ethylamino-2-propanol);
(1-((1,1-dimethylethyl)amino)-3-((2-methyl-1H-indol-4-yl)oxy)-2-propanol benzoate) (bopindolol);
(1-(2-exobicyclo[2.2.1]-hept-2-ylphenoxy)-3-[(1-methylethyl)-amino]-2-propanol HCl) (bornaprolol);
(o-[2-hydroxy-3-[(2-indol-3-yl-1,1-dimethylethyl)amino]propoxy]benzonitrile HCl) (bucindolol);
(α-[(tert.butylamino)methyl]-7-ethyl-2-benzofuranmethanol) (bufuralol);
(3-[3-acetyl-4-[3-(tert.butylamino)-2-hydroxypropyl]-phenyl]-1,1-diethylurea HCl) (celiprolol);
((±)-2-[2-[3-[(1,1-dimethylethyl)amino]-2-hydroxypropoxy]phenoxy]-N-methylacetamide HCl) (cetamolol);
(2-benzimidazolyl-phenyl(2-isopropylaminopropanol));
((±)-3'-acetyl-4'-(2-hydroxy-3-isopropylaminopropoxy)acetanilide HCl) (diacetolol);
(methyl-4-[2-hydroxy-3-[(1-methylethyl)aminopropoxy]]benzenepropanoate HCl) (esmolol);
(erythro-DL-1-(7-methylindan-4-yloxy)-3-isopropylaminobutan-2-ol);
(1-(tert.butylamino)-3-[0-(2-propynyloxy)phenoxy]-2-propanol (pargolol);
(1-(tert.butylamino)-3-[o-(6-hydrazino-3-pyridazinyl)-phenoxy]-2-propanol diHCl) (prizidilol);
((−)-2-hydroxy-5-[(R)-1-hydroxy-2-[(R)-(1-methyl-3-phenylpropyl)amino]ethyl]benzamide):
(4-hydroxy-9-[2-hydroxy-3-(isopropylamino)-propoxy]-7-methyl-5H-furo[3,2-g][1]-benzopyran-5-one) (iprocrolol);
((−)-5-(tert.butylamino)-2-hydroxypropoxy]-3,4-dihydro-1-(2H)-naphthalenone HCl) (levobunolol);
(4-(2-hydroxy-3-isopropylamino-propoxy)-1,2-benzisothiazole HCl);
(4-[3-(tert.butylamino)-2-hydroxypropoxy]-N-methylisocarbostyril HCl);
((±)-N-2-[4-(2-hydroxy-3-isopropyl aminopropoxy)-phenyl]ethyl-N'-isopropylurea) (pafenolol);
(3-[[(2-trifluoroacetamido)ethyl]amino]-1-phenoxypropan-2-ol);
(N-(3-(o-chlorophenoxy)-2-hydroxypropyl)-N'-(4'-chloro2,3-dihydro-3-oxo-5-pyridazinyl)ethylenediamine);
((±)-N-[3-acetyl-4-[2-hydroxy-3-[(1-methylethyl)amino]propoxy]phenyl]butanamide) (acebutolol);
((±)-4'-[3-(tert-butylamino)-2-hydroxypropoxy]spiro[cyclohexane-1,2'-indan]-1'-one) (spirendolol);
(7-[3-[[2-hydroxy-3-[(2-methylindol-4-yl)oxy]propyl]amino]butyl]thiophylline) (teoprolol);
((±)-1-tert.butylamino-3-(thiochroman-8-yloxy)-2-propanol) (tertatolol);
((±)-1-tert.butylamino-3-(2,3-xylyloxy)-2-propanol HCl) (xibenolol);
(8-[3-(tert.butylamino)-2-hydroxypropoxy]-5-methyl-coumarin) (bucumolol);
(2-(3-(tert.butylamino)-2-hydroxy-propoxy)benzonitrile HCl) (bunitrolol);
((±)-2'-[3-(tert-butylamino)-2-hydroxypropoxy-5'-fluorobutyrophenone) (butofilolol);
(1-(carbazol-4-yloxy)-3-(isopropylamino)-2-propanol) (carazolol);
(5-(3-tert.butylamino-2-hydroxy)propoxy-3,4-dihydrocarbostyril HCl) (carteolol);
(1-(tert.butylamino)-3-(2,5-dichlorophenoxy)-2-propanol) (cloranolol);
(1-(inden-4(or 7)-yloxy)-3-(isopropylamino)-2-propanol HCl) (indenolol);
(1-isopropylamino-3-[(2-methylindol-4-yl)oxy]-2-propanol) (mepindolol);
(1-(4-acetoxy-2,3,5-trimethylphenoxy)-3-isopropylaminopropan-2-ol) (metipranolol);
(1-(isopropylamino)-3-(o-methoxyphenoxy)-3-[(1-methylethyl)amino]-2-propanol) (moprolol);
((1-tert.butylamino)-3-[(5,6,7,8-tetrahydro-cis-6,7-dihydroxy-1-naphthyl)oxy]-2-propanol) (nadolol);
((S)-1-(2-cyclopentylphenoxy)-3-[(1,1-dimethylethyl)amino]-2-propanol sulfate (2:1)) (penbutolol);
(4'-[1-hydroxy-2-(amino)ethyl]methanesulfonanilide) (sotalol);
(2-methyl-3-[4-(2-hydroxy-3-tert.butylaminopropoxy)-phenyl]-7-methoxy-isoquinolin-1-(2H)-one);
(1-(4-(2-(4-fluorophenyloxy)ethoxy)phenoxy)-3-isopropylamino-2-propanol HCl);
((−)-p-[3-[(3,4-dimethoxyphenethyl)amino]-2-hydroxypropoxy]-β-methylcinnamonitrile) (pacrinolol);
((±)-2-(3'-tert.butylamino-2'-hydroxypropylthio)-4-(5'-carbamoyl-2'-thienyl)thiazole HCl) (arotinolol);
((±)-1-[p-[2-(cyclopropylmethoxy)ethoxy]phenoxy]-3-(isopropylamino)-2-propanol) (cicloprolol);
((±)-1-[(3-chloro-2-methylindol-4-yl)oxy]-3-[(2-phenoxyethyl)amino]-2-propanol) (indopanolol);
((±)-6-[[2-[[3-(p-butoxyphenoxy)-2-hydroxypropyl-]amino]ethyl]amino]-1,3-dimethyluracil) (pirepolol);
(4-(cyclohexylamino)-1-(1-naphtholenyloxy)-2-butanol);
(1-phenyl-3-[2-[3-(2-cyanophenoxy)-2-hydroxypropyl]aminoethyl]hydantoin HCl);
(3,4-dihydro-8-(2-hydroxy-3-isopropylaminopropoxy)-3-nitroxy-2H-1-benzopyran) (nipradolol);
α- and β-Adrenergic Blocking Agents:
((±)-1-tert-butylamino-3-[o-[2-(3-methyl-5-isoxazolyl)vinyl]phenoxy]-2-propanol) (isoxaprolol);
(1-isopropylamino-3-(4-(2-nitroxyethoxy)phenoxy)-2-propanol HCl);
(4-hydroxy-α-[[3-(4-methoxyphenyl)-1-methylpropyl]aminomethyl]-3-(methylsulfinyl)-benzmethanol HCl) (sulfinalol);
(5-[1-hydroxy-2-[[2-(o-methoxyphenoxy)ethyl]amino]ethyl]-2-methylbenzenesulfonamide HCl);
(5-[1-hydroxy-2-[(1-methyl-3-phenylpropyl)amino]ethyl]salicylamide HCl) (labetalol);
(1-((3-chloro-2-methyl-1H-indol-4-yl)oxy)-3-((2-phenoxyethyl)amino)-2-propanol-hydrogenmalonate) (ifendolol);
(4-(2-hydroxy-3-[(1-methyl-3-phenylpropyl)amino]-propoxy)benzeneacetamide);
(1-[3-[[3-(1-naphthoxy)-2-hydroxypropyl]-amino]-3,3-dimethyl-propyl]-2-benzimidazolinone);
(3-(1-(2-hydroxy-2-(4-chlorophenylethyl)-4-piperidyl)-3,4-dihydroxy)quinoxolin-2(1H)-one);
CNS-Acting Agents: clonidine; methyldopa;

Adrenergic Neuron Blocking Agents: guanethidine; reserpine and other rauwolfia alkaloids such as rescinnamine;

Vasodilators: diazoxide: hydralazine; minoxidil:

Angiotensin I Converting Enzyme Inhibitors:

1-(3-mercapto-2-methyl-1-oxopropyl)-L-proline (captopril);

(1-(4-ethoxycarbonyl-2,4(R,R)-dimethylbutanoyl)indoline-2(S)-carboxylic acid);

(2-[2-[[1-(ethoxycarbonyl)-3-phenyl-propyl]amino]-1-oxopropyl]-1,2,3,4-tetrahydro-3-isoquinoline carboxylic acid);

((S)-1-[2-[[1-(ethoxycarbonyl)-3-phenylpropyl]amino]-1-oxopropyl]octahydro-1H-indole-2-carboxylic acid HCl);

(N-cyclopentyl-N-(3-(2,2-dimethyl-1-oxopropyl)thiol-2-methyl-1-oxopropyl)glycine) (pivalopril);

((2R,4R)-2-(2-hydroxyphenyl)-3-(3-mercaptopropionyl)-4-thiazolidinecarboxylic acid);

(1-(N-[1(S)-ethoxycarbonyl-3-phenylpropyl]-(S)-alanyl)cis,syn-octahydroindol-2(S)-carboxylic acid HCl);

((−)-(S)-1-[(S)-3-mercapto-2-methyl-1-oxopropyl]indoline-2-carboxylic acid);

[1(S),4S]-1-[3-(benzoylthio)-2-methyl-1-oxopropyl]-4-phenylthio-L-proline;

(3-([1-ethoxycarbonyl-3-phenyl-(1S)-propyl]amino)-2,3,4,5-tetrahydro-2-oxo-1-(3S)-benzazepine-1-acetic acid HCl);

(N-(2-benzyl-3-mercaptopropanoyl)-S-ethyl-L-cysteine) and the S-methyl analogue;

(N-(1(S)-ethoxycarbonyl-3-phenylpropyl)-L-alanyl-L-proline maleate) (enalapril);

N-[1-(S)-carboxy-3-phenylpropyl]-L-alanyl-1-proline;

$N^2$-[1-(S)-carboxy-3-phenylpropyl]-L-lysyl-L-proline (lysinopril);

Calcium Channel Blockers:

α-[3-[[2-(3,4-dimethoxyphenyl)ethyl]methylamino]-propyl]-3,4-dimethoxy-α-(1-methylethyl)benzeneacetonitrile (verapamil);

1,4-dihydro-2,6-dimethyl-4-(2-nitrophenyl)-3,5-pyridinedicarboxylic acid dimethyl ester (nifedipine);

2-(2,2-dicyclohexylethyl)piperidine (perhexiline);

N-(1-methyl-2-phenylethyl)- -phenylbenzenepropanamine (prenylamine);

3-(aminosulfonyl)-4-chloro-N-(2,3-dihydro-2-methyl-1H-indol-1-yl)benzamide (indapamide);

(2'-(2-diethylaminoethoxy)-3-phenylpropiophenone (etafenone);

(4-[4,4-bis-(4-fluorophenyl)butyl]-N-(2,6-dimethylphenyl)-1-piperazineacetamide) (lidoflazine);

(2-(N-benzyl-N-methylamino)ethylmethyl-2,6-dimethyl-4-(m-nitrophenyl)-1,4-dihydro-3,5-pyridinedicarboxylate HCl) (nicardipine);

(N-(3,4-dimethoxyphenethyl)-2-(3,4-dimethoxyphenyl)-N-methyl-m-dithiane-2-propylamine-1,1,3,3-tetraoxide) (tiapamil);

(5,6-dimethoxy-2-(3-[(α-(3,4-dimethoxy)phenylethyl)-methylamino]propyl)phthalimidine) (falipamil);

(β-[(2-methylpropoxy)methyl]-N-phenyl-N-phenyl-methyl-1-pyrrolidineethanamine HCl monohydrate) (bepridil);

((±)-cis-3-(acetyloxy)-5-[2-(dimethylamino)ethyl]-2,3-dihydro-2-(4-methoxyphenyl)-1,5-benzothiazepin-4-(5H)-one) (diltiazem);

((E)-1-[bis-(p-fluorophenyl)methyl]-4-cinnamylpiperazine di HCl) (flunarizine);

(5-[(3,4-dimethoxyphenethyl)methylamino]-2-isopropyl-2-(3,4,5-trimethoxyphenyl)valeronitrile (gallopamil);

(ethylmethyl(2,3-dichlorophenyl)-1,4-dihydro-2,6-dimethyl-3,5-pyridinedicarboxylate (felodipine);

(isopropyl-2-methoxyethyl-1,4-dihydro-2,6-dimethyl-4-(3-nitrophenyl)-3,5-pyridinecarboxylate) (nimodipine);

(3-ethyl-5-methyl-1,4-dihydro-2,6-dimethyl-4-(3-nitrophenyl)-3,5-pyridine-dicarboxylate) (nitrendipine);

Other Antihypertensive Agents: aminophylline; cryptenamine acetates and tannates; deserpidine; meremethoxylline procaine; pargyline; trimethaphan camsylate; and the like, as well as admixtures and combinations thereof.

Typically, the individual daily dosages for these combinations can range from about one-fifth of the minimally-recommended clinical dosages to the maximum recommended levels for the entities when they are given alone. Coadministration is most readily accomplished by combining the active ingredients into a suitable unit dosage form containing the proper dosages of each. Other methods of coadministration are, of course, possible.

The renin-inhibitory novel peptides of the present invention may also be utilized in in vivo or in vitro diagnostic methods for the purpose of establishing the significance of renin as a causative or contributory factor in hypertension, hyperaldosteronism or congestive heart failure in a particular patient.

In the in vivo method, a novel peptide of the present invention is administered to a patient, preferably by intravenous injection, although parenteral administration is also suitable, at a hypotensive dosage level in a single dose of from 0.1 to 10 mg per kg of body weight, and the resulting transitory fall in blood pressure, if it occurs, indicates supranormal plasma renin levels.

In vitro methods which may be employed involve incubating a body fluid, preferably plasma, with a novel peptide of the present invention according to methods described in Boger et al., *J. Med. Chem.*, 1985, 28, 1789–1790.

Pepstatin may be employed in the methods described above as an active control (see, e.g., U.S. Pat. Nos. 3,784,686 and 3,873,681 for a description of the use of pepstatin in diagnostic methods of this type).

The following examples are intended to be representative and not limiting. $IC_{50}$ results were obtained according to the methods described in *J. Med. Chem.*, 1985, 28, 1789–1790.

EXAMPLE 1

Preparation of
BOC-Phe-His-ACHPA-NH-(3-quinuclidinyl)
($N^\alpha$-t-butoxycarbonyl-L-phenylalanyl-L-histidyl(3S,4S)-4-amino-5-cyclohexyl-3-hydroxypentanoyl-3-quinuclidinyl amide)

Step A. BOC-Phe-N-hydroxysuccinimide ester

To a cooled (−10° C.) solution of BOC-Phe (265 g; 1 mole) and N-hydroxysuccinimide (115 g; 1 mole) in acetonitrile (1.4 L) was added dicyclohexylcarbodiimide (DCC; 215 g; 1.05 moles) in 4 portions. The mixture was stirred at −10° C. (3 hrs), at 0° C. (17 hrs) and then at room temperature (3 hrs). The mixture was filtered to remove dicyclohexylurea, and the filtrate was concentrated, resulting in the product as an off-white crystalline solid (360 g), mp 149.5°–152° C.

Step B. BOC-Phe-His-OH

To a solution of NaHCO$_3$ (110 g) in H$_2$O (440 ml) was added a slurry of L-histidine hydrochloride monohydrate (55 g) in H$_2$O (400 ml). Dimethoxyethane (440 ml) and then a solution of BOC-Phe-N-hydroxysuccinimide ester (103 g) in dimethoxyethane (2 L) were added, and the mixture was stirred vigorously for 18 hrs. The mixture was filtered and concentrated, diluted with n-butanol (1 L) and acidified to pH 4.5 by the addition of 6N HCl. The aqueous layer was extracted with n-BuOH, and the combined organic layers were water-washed (4×100 ml). The mixture was concentrated and the residue slurried with ether and filtered, giving the product as a white solid (88.5 g), mp 185.5° C. (dec). TLC (4:2:1:1; n-BuOH:H$_2$O: HOAc:pyr), R$_f$=0.5. [α]$_D$20=26.6.

Step C. BOC-Phe-His(Boc)-OH

To a cooled (−5° C.; ice-bath) solution of BOC-Phe-His-OH (195 g) in methanol (3 L) were added Et$_3$N (135 ml) and then di-t-butyldicarbonate (118 g). The mixture was stirred (20 min) and then allowed to warm to room temperature over 2 hrs. The mixture was concentrated and the residue taken up in ether (3 L), washed with 25% NaHPO$_4$ solution (1 L), saturated NaCl solution, dried (MgSO$_4$) and filtered. Concentration and vacuum drying of the resulting solid gave the product (239 g). TLC (80:20:1:0.5; CH$_2$Cl$_2$:MeOH:H$_2$O:HOAc) R$_f$=0.5 [α]$_D$20=−2.5.

Step D. ACHPA-OEt hydrochloride

A cooled (ice-bath) solution of BOC-ACHPA-OEt (65 g) in absolute EtOH (400 ml) was stirred vigorously as anhydrous HCl was bubbled in. After 10 minutes, the cooling bath was removed and the addition of HCl continued until the temperature of the solution had reached 35° C. At this point, TLC showed complete conversion to product. The solution was concentrated to a thick oil, which was reconcentrated twice from toluene (2×100 ml) and dried in vacuo to a constant weight (55.5 g). TLC (90:10:1; CH$_2$Cl$_2$:MeOH:HOAc) R$_f$=0.4.

Step E. BOC-Phe-His(Boc)-ACHPA-OEt

To a cooled (ice-bath) solution of ACHPA-OEt hydrochloride (55.5 g) in CH$_2$Cl$_2$ (500 ml) were added Isp$_2$NEt (diisopropylethylamine; 6 ml) and then BOC-Phe-His(BOC)-OH (96.5 g), giving a clear solution. 1-Hydroxybenzotriazole hydrate (34 g) and additional Isp$_2$NEt (35 ml) were then added, followed by DCC (40 g) and a white precipitate formed slowly. The mixture was stirred (1 hr) and the ice bath was removed, with stirring being continued (18 hrs). The reaction mixture was filtered to remove dicyclohexylurea (38 g) and concentrated to a thick slurry, which was taken up in EtOAc (6 L) and 0.5 M citric acid solution (2 L). The layers were separated and the organic layer was washed with citric acid solution (2 L), H$_2$O (2×2 L), saturated NaHCO$_3$ (600 ml), H$_2$O (2×2 L) and brine, and dried (Na$_2$SO$_4$). The resulting solution was concentrated to a thick slurry, which was then crystallized from EtOAc, to give a white solid (97 g), mp 156.7°–157.8° C. TLC (4:1; EtOAc:hexanes) R$_f$=0.35. [α]$_D$20=−23.6.

Step F. BOC-Phe-His-ACHPA-NHNH$_2$ 410 g of hydrazine hydrate was added to a cooled (ice-bath) solution of BOC-Phe-His(BOC)-ACHPA-OEt (97 g) in methanol (1.5 L), and the reaction mixture was allowed to warm to room temperature over 3 hrs, before being cooled again (ice-bath) and stirred for 18 hrs. The mixture was concentrated to a thick slurry, then diluted with H$_2$O (500 ml) and filtered. The solid was rinsed with H$_2$O (3×500 ml) and then dissolved in boiling 95% EtOH (700 ml), filtered while hot, and cooled. The resulting solid was filtered and dried to give the product (74.5 g), mp 186.1°–187.7° C. TLC (3:1; CH$_2$Cl$_2$:MeOH) R$_f$=0.5. [α]$_D$20=−37.5.

Step G: BOC-Phe-His-ACHPA-NH-(3-quinuclidinyl)

To 20 ml dry, degassed dimethylformamide (DMF) was added 1.50 g (2.44 mmole) N$^α$-t-butoxycarbonyl-L-phenylalanyl-L-histidyle-(3S,4S)-4-amino-5-cyclohexyl-3-hydroxypentanoyl hydrazide (BOC-Phe-His-ACHPA-NHNH$_2$) and the solution was cooled under a nitrogen atmosphere to −30° C., with stirring. A freshly-prepared solution of HCl (g) in tetrahydrofuran (5.20 M; 4.69 ml, 24.4 mmole) was added to the cold reaction mixture and the pH of the solution was found to be within the desired range (0.5 to 1.5 pH).

Isoamyl nitrite (402 mg, 461 μl, 3.43 mmole) was added in four portions at −20° to −18° C. over 2-3 hours, while keeping the reaction mixture positive to a starch-iodide paper test throughout, and upon complete formation of the azide, a precooled (−20° C.) slurry containing 3-(R,S)-aminoquinuclidine dihydrochloride (2.43 g, 12.2 mmole) and triethylamine (3.70 g, 5.10 ml, 36.6 mmole) was added to the azide with vigorous stirring. The slurry was stirred at −20° C. for one hour, then stored in the freezer overnight, after which it was found that the pH dropped to 9.0 from 9.5–10.0 originally. The DMF was stripped off on a rotovap, with the residue being dissolved in n-butanol (175 ml), then washed consecutively with water (5×50 ml), with water washes 3 to 5 being back extracted with butanol, before all butanol extracts were combined, stripped and pumped under high vacuum to give 2.37 g of an oil.

The oil was chromatographed on a multiple pour packed gravity silica gel column (Whatman G60, 230–400 mesh) using CHCl$_3$:MeOH:H$_2$O:NH$_3$ (CMWA) (100:20:2:2) to 45 cm L×4.0 cm W, with the compound being dissolved in a 100:20:2:2 solution, the insolubles (39.46 mg) removed by filtration and found to be non-peptide material, and the filtrate charged to top of silica column. Elution proceeded with 1/1, 100:20:2:2/80:25:2.5:2.5 CHCl$_3$:MeOH:H$_2$O:NH$_3$ for 500 ml followed by 80:25:2.5:2.5.

The upper R$_f$(0.35; 85:25:2.5:2.5) diastereomer, Boc-phe-His-ACHPA-3-quinuclidinyl amide, cleanly eluted in cuts 63 to 66. Mixed (R,S) diastereomer cuts 69 to 89 were combined, stripped and freeze-dried from dioxane to give 1.00 g white solid. The lower R$_f$ (0.29; 85:25:2.5:2.5) diastereomer eluted in cuts 90 to 122 and required rechromatographing to purify.

The diastereomeric mixture Boc-phe-His-ACHPA-3-(R,S)-quinuclidinyl amide was fully characterized. Fast-atom bombardment (FAB) showed M$^+$+H=708, M$^+$=707 which fits exactly for C$_{38}$H$_{57}$N$_7$O$_6$, MWt=707.98, and elemental analysis showed: Calc'd: C, 64.47; H, 8.12; N, 13.85; Found: C, 62.89; H, 8.12; N, 13.65. IC$_{50}$=33 nM.

EXAMPLE 2

Preparation of
Boc-Phe-His-ACHPA-NH-(1-methylquinuclidinyl-3-yl) acetate salt
(N$^α$-t-butoxycarbonyl-L-phenylalanyl-L-histidyl-(3S,4S)-4-amino-5-cyclohexyl-3-hydroxy-pentanoyl-1-methylquinuclidium-3-yl amide acetate)

Boc-Phe-His-ACHPA-3-quinuclidine amide (36.51 mg, 51.5 μmoles) was dissolved in 200 μl CHCl$_3$ to which methyl iodide (3.53 μl, 56.7 μmole) had been added. After standing three days at room temperature, the solvent was evaporated, and the residue was dissolved in dilute acetic acid and passed through a column of BioRad AG 3X4A (300 mg). After lyophilizing the eluate, the title compound was isolated in 75% yield (34.95 mg). FAB(+)mass spec data (m/e):722(M+) Elemental analysis: Calc'd: C, 57.32; H, 7.50; N, 10.88; Found: C, 57.60; H, 7.03; N, 10.47.

NMR: consistent with structure. TLC:$R_f$=0.19(CMWA,60:40:3:6)E. Merck 60F silica plates. $IC_{50}$=38 nM.

EXAMPLE 3

Preparation of Boc-phe-His-ACHPA-NH-[1-(4-hydroxybutyl)-quinuclidinium-3-yl]acetate ($N^\alpha$-t-butoxycarbonyl-L-phenylalanyl-L-histidyl(3S,4S)-4-amino-5-cyclohexyl-3-hydroxypentanoyl-1-(4-hydroxybutyl)-quinuclidinium-3-yl amide acetate)

Boc-Phe-His-ACHPA-NH-(3-quinuclidinyl) (227 mg, 321 μmoles) was dissolved in 500 μl $CHCl_3$ to which 4-iodobutyl acetate (85 mg, 353 μmoles) had been added. After standing four days at room temperature, the solvent was evaporated and the crude product was chromatographed on Whatman G60 silica gel (3.0 cm×20.0 cm) using $CHCl_3$:MeOH:water:ammonia (CMWA) as an 60:40:3:6 eluent to yield pure Boc-Phe-His-ACHPA-NH-[1-(4-acetoxybutyl)-quinuclidinium-3-yl](188 mg, 198 μmoles).

Subsequent hydrolysis using $K_2CO_3$ (46.1 mg, 334 μmoles) in 10 ml MeOH in 45 minutes, filtration to remove solids, acidification of the filtrate with 0.5 ml glacial acetic acid and rotoevaporation to a colorless glass afforded 102 mg of Boc-Phe-His-ACHPA-NH-[1-(4-hydroxybutyl)quinuclidinium-3-yl]acetate (in 64% yield). The glass was lyophilized from 5 ml dioxane containing 5% water. FAB+mass spec data showed (m/e):780(M+). TLC:$R_f$=0.16 ($CHCl_3$:MeOH: $H_2O$:$NH_3$, 60:40:3:6 on EM Science 60$F_{254}$silica plates). NMR: consistent with structure. $IC_{50}$=33 nM.

EXAMPLE 4

Preparation of Boc-Phe-His-ACHPA-NH-(quinuclidinium-3-yl-1-oxide)

($N^\alpha$-t-butoxycarbonyl-L-phenylalanyl-L-histidyl-(3S,4S)-4-amino-5-cyclohexyl-3-hydroxypentanoyl-quinuclidinium-3-yl-1-oxide amide)

Boc-Phe-His-ACHPA-NH-(3-quinuclidinyl) (50.00 mg, 70.6 μmoles) was dissolved in 300 μl $CHCl_3$ to which m-chloroperbenzoic acid (12.2 mg, 70.6 μmoles) had been added. After standing overnight at room temperature, the oxidation product was isolated through chromatography on a 1.5 cm×15.0 cm column of Whatman G60 silica gel (230-400 mesh) using chloroform:methanol:water:ammonia (CMWA) as an 80:20:2:2 eluent to yield 40.4 mg (79% yield) of the title compound. FAB+mass spec data showed (m/e)724, (M+ +H) M+=723, consistent with $C_{38}H_{57}N_7O_7$. TLC:$R_f$=0.61 ($CHCl_3$:MeOH: $NH_3$:$H_2O$, 60:40:3:6 on E M Science 60$F_{254}$silica plates). NMR: consistent with structure. $IC_{50}$=20 nM.

EXAMPLE 5

Preparation of Boc-Phe-His-ACHPA-4-thiamorpholine

Boc-Phe-His-ACHPA-4-thiamorpholine was prepared according to the method of Example 1 with thiamorpholine replacing 3-aminoquinuclidine and the pH adjusted to 9–9.5 with triethylamine. The title compound was purified using chloroform:methanol:water (CMWA), 100:10:1 with Whatman G60 silica gel. FAB+mass spec data showed (m/e) M+ +H=685, M+=684. Spincoanalysis showed 0.982 Phe, 1.02 His, 93% peptide content. NMR: consistent with structure TLC:$R_f$=0.33 ($CHCl_3$:MeOH:$H_2O$/100:10:1; E M Science 60F silica plates). $IC_{50}$=19 nM.

EXAMPLE 6

Preparation of Boc-Phe-His-ACHPA-4-thiamorpholine-1-oxide

Boc-Phe-His-ACHPA-4-thiamorpholine (33 mg, 48.4 μl moles) was dissolved in 250 μl chloroform, chilled to −20° C. under $N_2$ while 1.0 equivalent m-chloroperbenzoic acid (9.19 mg, 53 μmole) was added, and the mixture was slowly warmed to room temperature. After fifteen hours, the solvent was evaporated in vacuo and the mixture was chromatographed on Whatman G60 silica gel, eluting with chloroform:methanol:water:acetic acid (CMWAcOH) in an 85:15:1.5:1.0 ratio. FAB+·MS showed M+ +H=701. NMR: consistent with structure. TLC:$R_f$=0.24 ($CHCl_3$:MeOH:$H_2O$:HOAc, 80:20:2:1, EM Science 60F silica plates). $IC_{50}$=67 nM.

EXAMPLE 7

Preparation of Boc-Phe-His-ACHPA-4-thiamorpholine-1,1-dioxide

The title compound was prepared according to Example 6 with 2.0 equivalents m-chloroperbenzoic acid replacing 1.0 equivalent thereof. FAB+ mass spec data (m/e):717 (M+ +H). NMR: consistent with structure. TLC:$R_f$=0.21 ($CHCl_3$:MeOH:$H_2O$:HOAC (CMWAcOH), 80:20:2:1, E M Science 60F silica plates). $IC_{50}$=55 nm.

EXAMPLE 8

Preparation of Boc-Phe-His-ACHPA-1-piperidine

Boc-Phe-His-ACHPA-1-piperidine was prepared according to the method of Example 1, with piperidine replacing 3-aminoquinuclidine and the chromatography solvent being 100:10:1, $CHCl_3$ MeOH:$H_2O$ (CMW). FAB+ mass spec data showed (m/e):667 (M+ +H). NMR: consistent with structure. TLC:$R_f$=0.27(CMW,85:15:1.5). $IC_{50}$=11 nM.

EXAMPLE 9

Preparation of Boc-Phe-His-ACHPA-NH-(2S-(+)-butyl) ($N^\alpha$-t-butoxycarbonyl-L-phenylalanyl-L-histidyl(3S,4S)-4-amino-5-cyclohexyl-3-hydroxypentanoyl-2S-(+)-butyl amide)

Boc-Phe-His-ACHPA-NH-(2S-(+)-butyl) was prepared according to the method of Example 1, with 2S-(+)-butyl amine replacing 3-aminoquinuclidine, and the chromatography solvent being 100:10:1, $CHCl_3$:MeOH:$H_2O$ (CMW). FAB+ mass spec data (m/e):655 (M+ +H). NMR: consistent with structure. TLC:$R_f$=0.51(CMA, 80:20:2). $IC_{50}$=32 nM.

EXAMPLE 10

Preparation of IPOC-Phe-His-ACHPA-NH-(3-quinuclidinyl)

IPOC-Phe-His-ACHPA-OEt is prepared according to the general stepwise solution coupling method starting from Boc-ACHPA-OEt and 40% TFA/CH$_2$Cl$_2$ deprotection, followed by mixed anhydride coupling to Boc-(DNP)His using isobutyl chloroformate. Subsequent deprotection with TFA followed by coupling to IPOC-Phe gives IPOC-Phe-His-ACHPA-OEt after 10% thiophenol/DMF treatment to remove DNP from histidine. Conversion to the hydrazide is effected in 50% hydrazine/methanol, and IPOC-Phe-His-ACHPA-NH-(3-quinuclidinyl) is prepared according to the method of Example 1, with IPOC-Phe-His-ACHPA-NHNH$_2$ replacing Boc-Phe-His-ACHPA-NNNH2.

IPOC-Phe was synthesized as the methyl ester by reaction of isopropyl chloroformate (7.72g, 63 mmole) with HCl-Phe-OMe (11.3 g, 63 mmol) and triethylamine in 500 ml methylene chloride at 0°-5° C. After warming to room temperature overnight, the reaction mixture was washed with 0.1M HCl (3×25 ml) and brine to yield 11.3 g IPOC-Phe-OMe after chromatography, with hydrolysis of the ester to IPOC-Phe proceeding under standard saponification conditions (dioxane-H$_2$O, 1:1 with 1.05 eq. NaOH) to give 8.95 g of IPOC-Phe as a white solid.

EXAMPLE 11

Preparation of Boc-Phe-His-ACHPA-NH-CH(2-butyl)-CH$_2$NH$_2$ (1-amino-2(S)-(Boc-Phe-His-ACHPA-amino)3(S)-methylbutane)

Step A. Boc-NH-CH-(2-butyl)-CH$_2$N$_3$(1-azido-2(S)-(Boc-amino)-3(S)-methylbutane)

A solution of L-isoleucinol (1.0 equiv.) in a mixture of water and dioxane was prepared and cooled to 0° C. Triethylamine (1.1 equiv.) was added followed by Boc$_2$O (1.1 equiv.). After stirring the mixture at 0° C. for 2.5 hours the reaction was diluted with ethyl acetate and washed with 1N HCl (twice), water (once), saturated sodium bicarbonate (once), brine (once), dried over magnesium sulfate and concentrated to an oil. This oil was dissolved in diethyl ether and the solution was cooled to 0° C. Triethylamine (2 equiv.) and then methanesulfonyl chloride (1.2 equiv.) were added to the solution. After 1 hour the reaction was partitioned between ethyl acetate and water. The ethyl acetate layer was washed with cold 1N HCl (once), water (once), saturated sodium bicarbonate (once), dried over magnesium sulfate and concentrated to a white solid. Fifty nine grams of this solid were dissolved in 500 ml of DMF followed by the addition of 20.5 grams of lithium azide. After stirring at room temperature for three days the reaction was heated to 50° C. for 2 hours then 10 grams more lithium azide was added and the reaction was held at 50° C. for several more hours until starting material had been consumed as indicated by silica gel TLC (3/2-hexanes/ethyl acetate). The reaction was concentrated then partitioned between methylene chloride and water. The organic layer was washed with water (once), brine (once), dried over magnesium sulfate and concentrated to a yellow oil weighing 49 grams. The desired product, 1-azido-2(S)-(Boc-amino)-3(S)-methylbutane, was isolated by silica gel chromatography using 4/1-hexanes/ethyl acetate to give 30 grams of the product as a crystalline solid. FAB(+) mass spec. data (M/e); 243 (M+1), 187, and 143. 300 MHz $^1$H-NMR NMR data (CDCl$_3$, TMS internal standard, ppm); 0.9 (m, 6H), 1.45 (s, 9H), 3.4 (m, 2H), 3.6 (m, 1H), 4.6 (d, 1H).

Step B. Boc-Phe-His-ACHPA-NH-CH(2-butyl)CH$_2$N$_3$ (1-azido-2(S)-(Boc-Phe-His-ACHPA-amino)-3(S)-methylbutane)

Four and a half grams of the product of Step A was dissolved in 40 ml of methylene chloride. The solution was cooled to 0° C. then 40 ml of trifluoroacetic acid was added. After 30 minutes at 0° C. the reaction was allowed to warm to room temperature and stirred an additional 30 minutes. The reaction was concentrated then reconcentrated from toluene twice to give 1-azido-2(S)-amino-3(S)-methylbutane trifluoroacetic acid salt as a yellow oil. Ten grams of Boc-Phe-His-ACHPA-NHNH$_2$, prepared by the method of Example 1, was dissolved in 125 ml of DMF. The solution was cooled to −30° C. and the pH was adjusted to 2 with 10% HCl. One equivalent (2.2 ml) of isoamylnitrite was added and the reaction was stirred at −30° C. for 3 hours. The 1-azido-2(S)-amino-3(S)-methylbutane trifluoroacetic acid salt was dissolved in 10 ml of DMF and added to the reaction. The pH of the reaction was maintained at 10 by the addition of diisopropylethylamine. The reaction was allowed to warm to −5° C. and held at that temperature for 3 days. The reaction was concentrated then diluted with ethyl acetate, washed with water three times, dried over magnesium sulfate and concentrated to a white foam. The desired product, 1-azido-2(S)-(Boc-Phe-His-ACHPA-amino)-3(S)-methylbutane, was isolated in 84% yield by silica gel chromatography using a 1/9-methanol/ethyl acetate mobile phase. FAB(+) mass spec. data m/e; 724 (M+1). 300 MHz $^1$H NMR data (CD$_3$OD, TMS internal standard, ppm); 0.9 (m, 6H), 1.4 (s, 9H), 2.2 (d, 2H), 6.9 (s, 1H), 7.3 (m, 5H), 7.6 (s, 1H).

Step C. Boc-Phe-His-ACHPA-NH-CH(2-butyl)CH$_2$NH$_2$ (1-amino-2(S)-(Boc-Phe-His-ACHPA-amino)-3(S)-methylbutane)

1-Azido-2(S)-(Boc-Phe-His-ACHPA-amino)-3(S)-methylbutane (9.92 grams, prepared as in Step B) was dissolved in 100 ml of methanol. Acetic acid (2.4 ml) and 10% Pd/C (1 gram) were added. The reduction was run wtih 40 psig hydrogen pressure and shaking at room temperature overnight. The reaction was filtered, concentrated and then reconcentrated from toluene twice. The residue was dissolved in n-butanol and washed with saturated sodium bicarbonate (twice), water (once) and concentrated to an oil. The product was isolated (3 grams) by chromatography using a Sephadex LH-20 stationary phase and methanol mobile phase followed by silica gel as the stationary phase and 80/10/1-CHCl$_3$/MeOH/NH$_3$ as a mobile phase. FAB(+) mass spec. data m/e; 698 (M+1). 300 MHz $^1$H NMR data (CD$_3$OD, TMS internal standard, ppm); 0.9 (m, 6H), 1.4 (s, 9H), 2.3 (d, 2H), 2.6 (dd, 1H), 6.9 (s, 1H), 7.25 (m, 5H), 7.6 (s, 1H). IC$_{50}$=33nM.

EXAMPLE 12

Preparation of
Boc-Phe-His-ACHPA-NHCH(2-butyl)-CH$_2$N(CH$_3$)$_2$
(1-dimethylamino-2(S)-(Boc-Phe-His-ACHPA-amino)-
3(S)-methylbutane)

1-Amino-2(S)-(Boc-Phe-His-ACHPA-amino)-3(S)-methylbutane (100 mg, prepared as in Example 11) was dissolved in 3 ml methanol. powdered 3A° molecular sieves and 52 microliters of 37% formalin were added. After 10 minutes 42 mg of NaBH$_3$CN was added and the reaction was stirred at room temperature overnight. The reaction was then filtered, concentrated, diluted with ethyl acetate, washed with water (twice) and brine (once), dried over sodium sulfate and concentrated to a colorless glass. The desired product was isolated (56 mg) by chromatography over silica gel using a 80/10/1-CHCl$_3$/MEOH/NH$_3$ mobile phase. FAB(+) mass spec. data m/e; 726 (M+1). 300 MHz $^1$H NMR (CD$_3$OD, TMS internal standard, ppm); 0.9 (m, 6H), 1.4 (s, 9H), 2.3 (s, 6H), 6.9 (s, 1H), 7.25 (m, 5H), 7.6 (s, 1H). IC$_{50}$=5nM.

EXAMPLE 13

Preparation of
Boc-Phe-His-NHCH(cyclohexylmethyl)-
CH(OH)CH$_2$CH$_2$OMe

Step A. The acetonide of Boc-ACHPA-OEt

Boc-ACHPA-OEt (10 gm, 30 mmol) was dissolved in 2-methoxypropane (15 ml), POCl$_3$ (5 drops) was added and the solution was stirred at room temperature until the reaction was determined complete by $^1$H NMR (2-3 days), at which time the solution was neutralized with Et$_3$N, and concentrated at room temperature. The solid residue was dissolved in ether, washed with aqueous citric acid, aqueous NaHCO$_3$ and finally with water until the washes were neutral, then the ether layer was dried (MgSO$_4$), filtered, and concentrated to give 12 gm. of crude acetonide, which was purified by flash chromatography (hexane-ether, 9:1 to 8:2) over silica gel (230-400 mesh) to yield 9.03 gm. of product. An analytical sample was prepared by crystallization from ether, 91°-92°.

Step B. Reduction of Boc-ACHPA-OEt acetonide to the alcohol

The acetonide of Boc-ACHPA-OEt from Step A, (7.67 gm, 20 mmol) was dissolved in toluene (20 ml) cooled to 0° C. and 1.5M Dibal in toluene (30.7 ml, 46 mmol) was added dropwise keeping the temperature at 0° C. After 30 minutes, the reaction was added to ice, extracted with ether, and the ether extract was treated with Na+K+ tartrate. The gel which precipitated was filtered in order to separate the ether layer to give 6.64 gm. of solid. Flash chromatography (ether-hexane 1:1) yielded 5.65 gm. of the desired alcohol.

Step C. The mesylate of

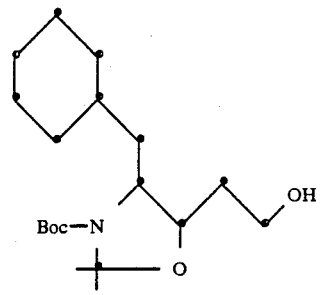

The alcohol from Step B (5.65 gm. 16.5 mmol) was dissolved in CH$_2$Cl$_2$ (20 ml), cooled to 0° C. and treated with Et$_3$N (2.51 gm., 24.8 mmol), followed by the cautious addition of CH$_3$SO$_2$Cl (2.84 gm, 1.92 ml, 24.8 mmol). The reaction mixture was placed in the refrigerator overnight, then diluted with ether and water, washed with aqueous citric acid, aqueous NaHCO$_3$, and finally water until neutral, then dried (MgSO$_4$) and concentrated. Flash chromotography (hexane-ether 1:1) over silica gel yielded 6.74 gm of the mesylate.

Step D. Methyl ether from the mesylate of Step C

Sodium (72.5 gm, 3.15 mmol) was dissolved in methanol (20 ml) and the mesylate from Step C, (0.87 gm, 2.1 mmol) was added and refluxed until the reaction was complete. The mixture was acidified with HOAc and concentrated, with the residue being dissolved in ether and washed with aqueous NaHCO$_3$ followed by water, dried (MgSO$_4$) and concentrated to give 0.60 gm of crude product. Flash 0.41 gm. of the methyl ether.

Step E. Cleaving of the acetonide and Boc-protection of the ether of Step D

The acetonide 4a (0.41 gm) was dissolved in ethyl acetate (30 ml), cooled to −20° C. initially and HCl gas was bubbled in for 30 minutes, keeping the temperature at 0° C. The reaction mixture was purged with N$_2$ to remove excess HCl then concentrated at room temperature in vacuo to give the HCl salt of ACHPA methyl ether (0.31 gm), which was used in the next step without further purification.

Step F. Boc-Phe-His(DNP)-ACHPA methyl ether

This tripeptide ether was prepared by a one-step coupling of the Boc-Phe-His(DNP)OH dipeptide fragment with the ACHPA ether from Step E. An active ester was prepared by dissolving Boc-Phe-His(DNP)OH (0.739 gm, 1.3 mmol) and N-hydroxysuccimide (0.150 gm, 1.3 mmol) in CH$_2$Cl$_2$ (15 ml) at room temperature and adding EDC (0.249 gm, 1.3 mmol). Coupling was achieved by adding the HCl salt of ACHPA -methyl ether (0.31 gm, 1.23 mmol) to the active ester and adjusting the pH to 7 with diisopropylethylamine (15 drops). After standing overnight at room temperature the reaction mixture was concentrated and redissolved in EtOAc, washed with water, aqueous citric acid, aqueous NaHCO$_3$ and finally water again, then, dried (MgSO$_4$) and concentrated to give a yellow colored solid which was purified by flash chromatography (CH$_2$Cl$_2$ - MeOH, 97:3 to 95:5) to yield 0.57 gm of product.

Step G. Boc-Phe-His-ACHPA Methyl Ethers

The DNP derivative of the title compound from Step F, was dissolved in CH$_2$Cl$_2$ (5 ml) and treated with thiophenol (1.4 ml) for 1.5 hours at room temperature then concentrated in vacuo and purged with EtOH to remove the last traces of thiophenol. Flash chromatography then yielded the pure producted methyl ether (0.24 gm), then finally 0.17 gm (99% pure) of methyl ether,

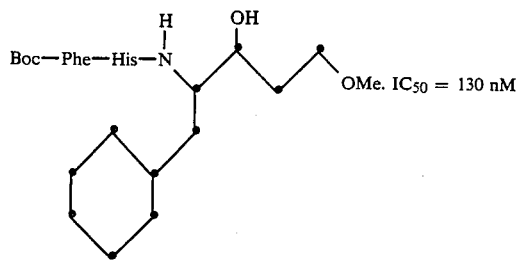

EXAMPLE 14

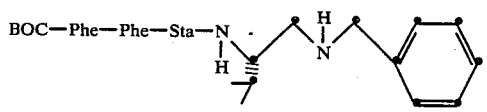

Step A.

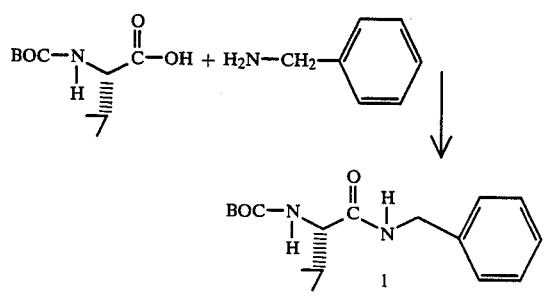

N-Methylmorpholine (9.14 ml, 83.2 mmole), and BOC-leucine hydrate (20.0 g, 83.2 mmole) were dissolved in CH$_2$Cl$_2$ (200 ml), the solution cooled to $-5°$ C. and isobutylchloroformate (10.8 ml, 83.2 mmole) was added. The resulting solution was stirred 15 min; benzylamine (10.9 ml, 99.8 mmole) was added and the solution was again stirred for 15 min.

This solution was warmed to 25° C. (30 min.), dichloromethane (300 ml) added, and the organic layer was washed with 10% citric acid (2×150 ml), water (1×150 ml), 10% sodium bocarbonate (2×150 ml), and brine (2×150 ml), then dried over Na$_2$SO$_4$, and filtered. The filtrate was evaporated under reduced pressure and the residue was dried at 25° C. in a vacuum oven to give 24.75 g (93% yield) of compound 1 as a waxy colorless solid.
Step B.

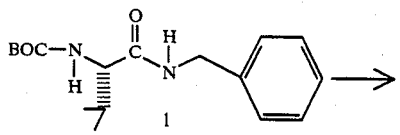

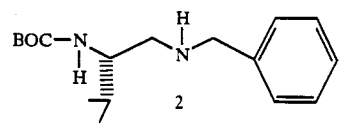

Compound 1 from Step A (1.0 g, 3.1 mmole) was dissolved in tetrahydrofuran (6.25 ml) and the solution cooled to $-25°$ C. Diborane (6.25 ml of 1M tetrahydrofuran solution, 6.25 mmole) was added dropwise, the solution was stirred 48 hours at $-10°$ C., and methanol (5 ml) was added. The reaction was stirred at 25° C. for 16 hours, the solvent was removed under reduced pressure, and the residue was treated with methanol and restripped (3X). Flash chromatography of the final residue using silica gel, eluted with 35% ethyl acetate in hexane, gave 380 mg (40% yield) of protected amine 2 as a light yellow oil.
Step C.

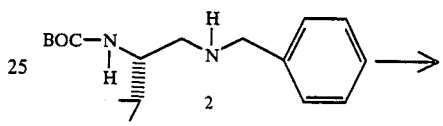

Protected amine 2 (540 mg, 1.8 mmol) was dissolved in ethyl acetate (10 ml), the solution was cooled to 0° C. and saturated with HCl (g), then stirred for 15 min and the solvent was removed in vacuo. The residue was treated with ethyl acetate and restripped (4X) to give a quantitative (490 mg) yield of diamine dihydrochloride 3 as an off-white solid.
Step D.

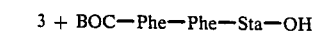

BOC-Phe-Phe-Sta-OH (240 mg, 0.421 mmole), diamine dihydrochloride 3 (130 mg, 0.466 mmole), 1-hydroxybenzotriazole hydrate (HBT) (62.9 mg, 0.466 mmole), and 1-ethyl-3-(3-dimethylaminopropyl) carbodiimide hydrochloride (EDC) (895 mg, 0.466 mmole) were dissolved in degassed dimethylformamide (4 ml) under a nitrogen atmosphere, and the pH of the solution was adjusted to 9.0–9.5 with triethylamine (0.30 ml, 2.16 mmole). After stirring 24 hours, a second portion of HBT (7 mg, 7.052 mmole) and EDC (9 mg, 0.047 mmole) was added, the suspension was stirred 6 hours and the dimethylformamide was removed in vacuo.

The residue was treated with 10% citric acid and extracted with ethyl acetate (3X), with the organic layers being combined, washed once with H₂O, 10% aqueous sodium bicarbonate (2X), and brine (1X), then dried over MgSO₄, filtered, and stripped under reduced pressure to give 280 mg of a white foam. Flash chromatography on silica gel with 150/10/1/1 of dichloromethane/methanol/water/acetic acid gave the desired product 5 (200 mg, 62.7% yield) as a white foam. IC₅₀ 2 μM.

EXAMPLE 15

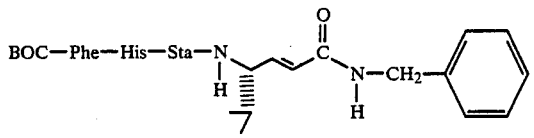

Step A.

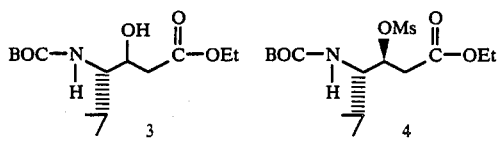

To an ice cold, stirred solution of BOC-statine ethyl ester 3 (2.60 g, 8.57 mmole) in 10 ml of pyridine was added via syringe 0.66 ml (8.57 mmole) of trifluoromethane sulfonyl chloride. Within minutes, pyridinium hydrochloride precipitated from solution, and the reaction mixture was protected from moisture and allowed to stand at room temperature overnight.

The next morning, the reaction mixture was filtered and the filtrate concentrated to give a light orange oil, which was further filtered through 5–10 g of silica gel (ether elution) to give 3.0 g of a pale yellow oil, which was used immediately without further purification, in that resulting compound 4 is prone to hydrolysis back to 3.

Step B.

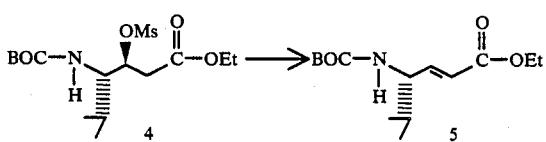

1,5-Diazabicyclo[4.3.0]non-5-ene (DBN) (0.94 ml, 7.54 mmole) was added in one portion to a stirred solution of compound 5 (2.9 g, 6.85 mmole) in 25 ml of dry tetrahydrofuran, resulting in a slightly exothermic reaction. Within minutes, a thick white precipitate formed, with stirring continuing for several hours more before the reaction mixture was filtered and the filtrate was concentrated in vacuo.

The residual oil was partitioned between ether and 10% citric acid solution, with the organic phase being washed with citric acid (2×40 ml) and brine, then dried (Na₂SO₄) and concentrated. Flash chromatography on silica gel (7:3 hexane-ethyl acetate elution) provided the analytical sample as an oil (1.6 g). ir; pmr(CDCl₃): olefinic protons 5.9 (d, J=17), 6.83 (d×d, J=17 and 5). J (coupling constant) is consistent with trans double bond.

Step C.

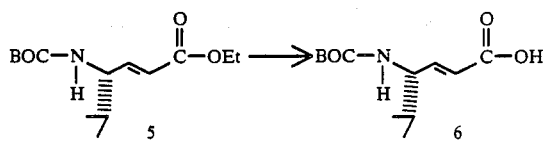

The α,β-unsaturated ester 5 (1.5 g, 5.3 mmole) was dissolved in 20 ml of water/dioxane (1:1 v/v) and treated with 7 ml (1.3 equivalents) of 1M sodium hydroxide solution. After 3 hours, another 1 ml of 1M sodium hydroxide solution was added, and after one more hour of reaction time, dioxane was removed in vacuo and the alkaline aqueous residue was diluted to 25 ml with water and washed with ether (2×25 ml). The aqueous phase was acidified with 10% citric acid and extracted with ether and chloroform, and the combined organic extracts were washed with brine and dried (Na₂SO₄), with concentration under reduced pressure affording 1.46 g of acid 6.

Step D.

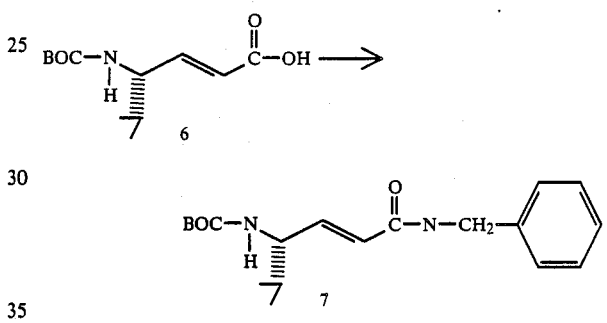

The acid 6 (400 mg, 1.6 mmole) was dissolved in 4 ml of methylene chloride under nitrogen and N-methylmorpholine (0.18 ml, 1.6 mmole) was added and the solution cooled to −5° C. Isobutylchloroformate (0.21 ml, 1.6 mmole) was added and 15 minutes later, 0.22 ml (1.92 mmole) of benzylamine was added to the reaction mixture. After 30 minutes more at −5° C., the reaction mixture was warmed to room temperature, stirred 1 more hour and diluted with 70 ml of methylene chloride. The organic phase was washed, in succession, with 10% citric acid (2×30 ml), saturated sodium bicarbonate solution (2×30 ml), and brine, and the organic extracts were dried (Na₂SO₄) and concentrated to yield 460 mg of a white solid identified as Boc-amide 7.

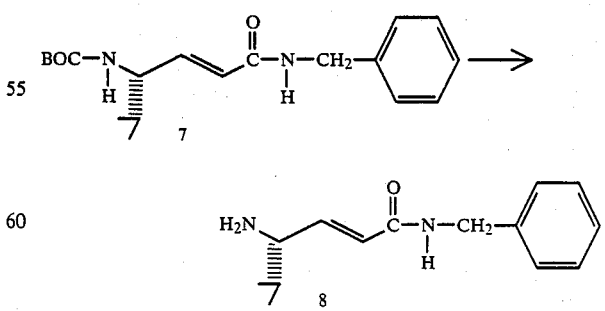

The BOC-amide 7 (240 mg, 0.69 mmole) was dissolved in 20 ml of ethyl acetate, cooled to 0° C. and treated with a stream of hydrogen chloride gas for 1 hour, with solvent and excess reagent being removed under reduced pressure to afford 200 mg of a pale yellow solid 8.
Step F.

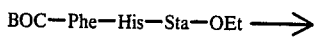

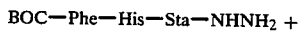

Separately, the tripeptide ester BOC-Phe-His-Sta-OEt 1 (520 mg, 0.89 mmole) was dissolved in 4 ml of methanol and treated with 2 ml (62 mmole) of 95% hydrazine. After 10 minutes at room temperature, the reaction mixture was concentrated in vacuo (0.1 Torr) to afford 420 mg of hydrazide 2 as a tan powder.
Step G.

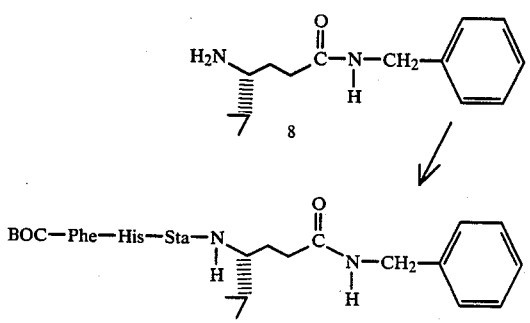

The hydrazide 2 (240 mg, 0.42 mmole) was dissolved in 2 ml of dry dimethylformamide under nitrogen, cooled to −20° C. and the pH of the solution adjusted to approximately 0.5–1.0 with tetrahydrofuran saturated with hydrogen chloride. Isoamyl nitrite was then added in 50 μl increments at 15–20 minute intervals until a positive potassium iodide-starch test was obtained (250 μl total) and the amine salt 8 (190 mg, 0.67 mmole), which had been dissolved in 2 ml of dimethylformamide, was added to the reaction mixture.

Upon completion of the addition, the pH of the reaction mixture was adjusted to 7.5–8.0 with triethylamine and the reaction mixture is allowed to stir at −20° C. for 20 hours. At the end of this period, the reaction mixture was filtered, the filtrate was concentrated, and the resulting residue partitioned between ethyl acetate and water. The organic phase was washed, in succession, with 10% citric acid solution (2×50 ml), 50% sodium bicarbonate solution (2×50 ml), and brine, and the organic extracts were dried (Na₂SO₄) and rotoevaporated to yield 140 mg of a yellow semi-solid. Chromatography on silica gel (80:10:1 CHCl₃-ethanol-ammonia elution) yielded the title compound as a pale yellow solid. IC$_{50}$=110nM.

EXAMPLE 16

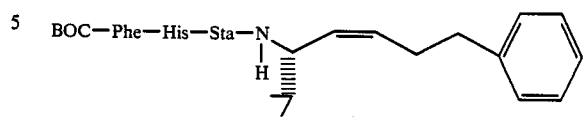

Step A.

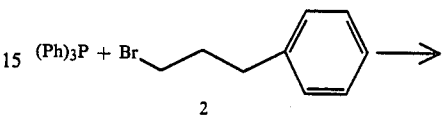

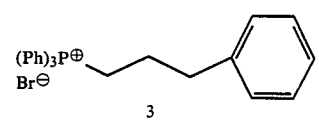

3-Phenyl-1-bromopropane (19 ml, 72.8 mmole) and triphenyl phosphine (19.11 g, 72.8 mmole) were combined at room temperature, and immersed in a preheated oil bath at 150° C., with heating continuing for 1.5 hours at 150°–160° C. The resulting dark brown solution was cooled and diluted with 200 ml of acetone, then the acetone was decanted and the residue triturated with hot ethyl acetate. The resulting off-white solid was further washed with ethyl acetate to give 24.2 g of compound 3 as a white powder, m.p. 203°–207° C.
Step B.

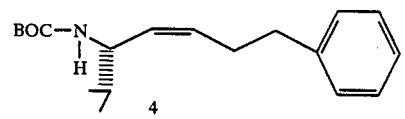

A rapidly-stirred suspension of 3 (1.82 g, 3.95 mmole) in 15 ml of dry tetrahydrofuran was treated dropwise under nitrogen at 0° C. with n-butyl lithium (1.4N, 2.82 ml, 3.95 mmole). The resulting homogeneous, dark brown mixture was cooled to −78° C. and treated with 5 ml of tetrahydrofuran containing 0.5 g (2.32 mmole) of BOC-leucine aldehyde 1, then after four hours at −78° C., the reaction mixture was warmed back to −10° C. for 1 hour. The mixture was quenched with saturated ammonium chloride solution, and partitioned between ether and brine.

The organic phase was washed with 10% citric acid solution (3×20 ml), 50% sodium bicarbonate solution (3×20 ml), and brine, with rotoevaporation of the dried (Na₂SO₄) extracts affording 0.42 g of crude product as a yellow oil (the analytical sample was obtained by chromatography of the crude product on silica gel (hexane-ethyl acetate 9:1 elution)).
Step C.

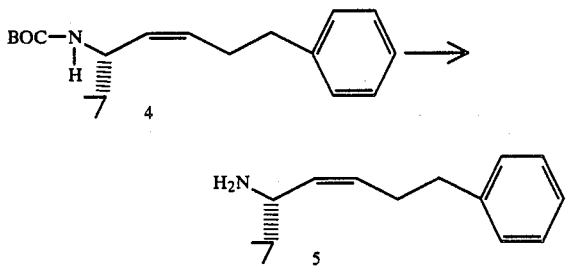

The BOC-olefin 4 (410 mg, 1.29 mmole) was dissolved in 20 ml of ethyl acetate, cooled to 0° C., and treated with hydrogen chloride gas for 1 hour. Concentration of the reaction mixture in vacuo and under high vacuum gave the HCl salt 5 as a beige solid (310 mg).
Step D.

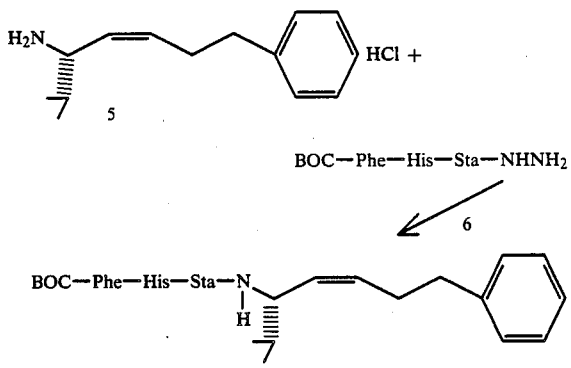

BOC-Phe-His-Sta-NHNH$_2$ (240 mg, 0.42 mmole) [obtained as described in Example 15, Step F] was converted to the corresponding BOC-Phe-His-Sta-N$_3$ (azide) with isoamylnitrite (200 μl) [using identical reaction conditions as described in Example 15, Step G] and the amine salt 5 (160 mg, 0.63 mmole) was added [with the reaction being carried out and worked-up as described in Example 16, Step G]. The analytical sample (70 mg) is obtained after silica gel chromatography (80:10:1 CHCl$_3$-ethanolammonia elution) as a pale yellow solid. IC$_{50}$=20nM.

EXAMPLE 17

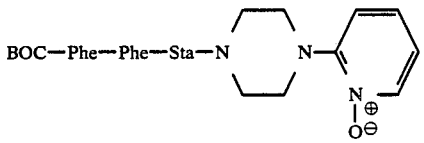

Step A.

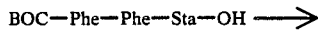

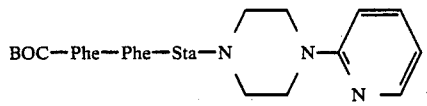

To a solution of 1 ml of dimethylformamide at 0° was added, in succession, BOC-Phe-Phe-Sta-OH (114 mg, 0.2 mmole), 2-pyridylpiperazine (33.5 μl, 35 mg, 0.22 mmole) diphenylphosphorylazide (47.5 μl, 60.7 mg, 0.22 mmole), and sodium bicarbonate (84 mg, 1 mmole), and the resulting suspension was protected from moisture and stirred at 0° for 12 hoursN More diphenylphosphorylazide was added (47.5 μl, 0.22 ml), with stirring continuing at 0° C. for 2 days, at which time the reaction mixture was filtered and the filtrate concentrated in vacuo. The residue was chromatographed on silica gel (90:10:1:0.1 chloroform/methanol/water/acetic acid elution) to give 125 mg of the analytical sample as a white solid.
Step B.

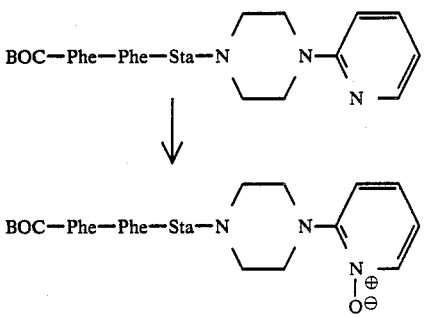

The tri-peptide of Step A (41 mg, 0.06 mmole) was dissolved in 5 ml of chloroform and the resulting solution treated with 20 mg of tech. grade m-chloroperbenzoic acid (85%) and allowed to stand for 19 hours at room temperature. The solvent was removed under reduced pressure and the residue was chromatographed on silica gel (chloroform-ethanolammonia 80:10:1 elution), with a material with R$_f$ value of 0.24 being isolated to provide the analytical sample as a white solid (32 mg)N IC$_{50}$=2 μM.

EXAMPLE 18

Preparation of
Boc-Phe-His-ACHPA-NHCH(2-butyl)CH$_2$N(CH$_3$)$_3$ di-acetate salt
(1-trimethylamino-2(S)-(Boc-Phe-His-ACHPA-amino)-3(S)-methylbutane di-acetate salt)

(1-Dimethylamino-2(S)-(Boc-Phe-His-ACHPAamino)-3(S)-methylbutane) (1.60 g, prepared as in Example 12) was dissolved in 15 ml of dimethylformamide (DMF), cooled to 0° C., and triethylamine (306 % μl) and di-tert-butyl dicarbonate (532 μl) were added in sequence. After stirring at 0° C. for three hours, the reaction was concentrated under vacuum and the residue was dissolved in ethyl acetate and washed with water and brine and dried over Na$_2$SO$_4$, then concentrated under vacuum. After dissolving in acetonitrile and reconcentrating, (1-dimethylamino-2(S)-(Boc-Phe-(N$^{im}$-Boc)His-ACHPA-amino)-3(S)-methylbutane was obtained as a white foam, weighing 1.88 g.

A portion of this foam (1.58 g) was dissolved in 3.5 ml of chloroform, methyl iodide (143 μL) was added, and the reaction was allowed to proceed (protected from light) at room temperature for four days, at which time the reaction mixture was concentrated, dissolved in acetonitrile and reconcentrated. The residue was then dissolved in 3 ml of methanol and saturated with ammonia gas at room temperature, and the flask was stoppered and stirred at room temperature for four hours. This reaction mixture was concentrated, then reconcentrated from acetonitrile to give a residue weighing 1.74 g, which was dissolved in 90 ml of acetonitrile, and to which diethyl ether was added to precipitate 1.4 g of 1-trimethylamino-2(S)-(Boc-Phe-His-ACHPA-amino)-3(S)-methylbutane iodo salt.

The iodo salt was dissolved in 20 ml of 5% acetic acid in water and the resulting solution was passed through an anion exchange resin (Biorad AG3-4A, converted to the acetate form), with the desired product, 1-trimethylamino-2(S)-(Boc-Phe-His-ACHPA-amino)-3(S)-methylbutane di-acetate salt being eluted from the resin (additional 5% acetic acid was used to ensure complete elution). The solvent was removed by freeze drying, and the product was reconcentrated from acetonitrile and toluene several times to remove remaining water and acetic acid, giving 1.28 g of the di-acetate salt as a white foam. FAB(+) mass spec. date (m/e); 740 (molecular ion). 300 $^1$H-NMR data (CD$_3$OD, TMS internal standard, ppm); 0.95 (m,6H), 1.35 (s,9H), 1.95 (s,6H), 2.3 (m,2H), 3.15 (s,9H), 6.9 (s,1H), 7.25 (m,H), 7.6 (s,1H). IC$_{50}$=15nM.

EXAMPLE 19

Preparation of
Boc-Phe-His-ACHPA-NHCH(2-butyl)-
CH$_2$N(CH$_3$)$_2$(CH$_2$)$_2$OH acetate salt
(1-(hydroxyethyldimethyl)amino-2(S)-(Boc-Phe-His-ACHPA-amino)-3(S)-methylbutane acetate salt)

104 mg of (1-dimethylamino-2(S)-(Boc-Phe-(N$^{im}$-Boc)His-ACHPA-amino)-3(S)-methylbutane, prepared as in Example 18, was dissolved in 250 μL of chloroform, 2-iodoethanol (12 μL) was added and the reaction was allowed to stir at room temperature (protected from light) for one day. The reaction mixture was heated (to as high as reflux) and more 2-iodoethanol (to a total of 64 μL) was added over several days until the reaction was judged to be essentially complete by TLC analysis (silica gel, 80/10/1-CHCl$_3$/CH$_3$OH/NH$_3$), and it was concentrated and reconcentrated from acetonitrile.

The residue was dissolved in 2 ml of methanol and saturated with ammonia gas at room temperature, then the flask was stoppered and the reaction was stirred at room temperature for five hours. The resulting mixture was concentrated and reconcentrated from acetonitrile, and the residue was dissolved in 5% acetic acid in water (a little extra acetic acid was added to completely dissolve the residue), then passed through an anion exchange column (Biorad AG3-4A converted to the acetate form), with the column being further rinsed with 5% acetic acid to ensure complete elution of the product.

The eluent was freeze dried, and 1-(hydroxyethyl dimethyl)amino-2(S)-(Boc-Phe-His-ACHPA-amino)-3(S)-methylbutane acetate salt was isolated from the residue by silica gel chromatography (80/30/3/3-CHCl$_3$/CH$_3$OH/H$_2$O/NH$_3$), passing the fraction containing the desired product through another anion exchange column (Biorad AG3-4A converted to the acetate form), as before, and finally precipitating from acetonitrile/diethylether to give a total of 33 mg as a solid. FAB(+) mass spec. data (m/e); 770 (molecular ion). 300 $^1$H NMR data (CH$_3$OD, TMS internal standard, ppm); 0.95 (m,6H), 1.4 (s,9H), 1.9 (s,3H), 2.3 (d,2H), 3.2 (s,6H), 6.9 (s,1H), 7.25 (m,5H), 7.6 (s,1H). IC$_{50}$=10 nM.

EXAMPLE 20

Intravenous and Oral Activity Testing of Novel Renin Inhibitors

The efficacy of the renin inhibitors of Examples 2 and 3 was tested using trained, conscious female, Rhesus monkeys (2.5–4.0 kg) instrumented with chronic arterial and venous access ports.

In these experiments, the plasma renin activity (PRA) of these monkeys was elevated and mean arterial blood pressure (MAP) was made partially renin-dependent by volume depletion with a low sodium diet (1 week) and administration of furosemide (2.5mg/kg, intramuscularly (i.m.)) the evening before the experiment. Test compounds were administered intravenously (I.V.) via the venous port or orally using an infant nasogastric feeding tube. Before and at various times following challenge with the test compound, changes in PRA (using standard methods and a commercially-available RIA kit for Angiotensin I Clinical Assays)).

Intravenous administration of the compound of Examples 2 (0.41 and 1.64 mg/kg) and 3 (0.24 and 1.44 mg/kg) caused 90–100% inhibition of PRA for a minimum of 3 to 6 hours. Maximum decreases in MAP were −20 and −30 mmHg for the compound of Example 3 and −9 and −38 mmHg for the compound of Example 2 at low and high doses respectively.

Oral administration of the compound of Example 3 at 10 mg/kg to two monkeys caused a 72–86% inhibition of PRA, with an onset of the response within 30 minutes and no signs of reversal at 6 hours. Decreases in MAP (−5 mmHg) were observed at this dose.

Both compounds, therefore, demonstrated effective renin inhibition with relatively long duration of action following intravenous or oral administration to conscious, sodium-deficient Rhesus monkeys.

The claims of the invention follow.

What is claimed is:

1. A compound of the formula:

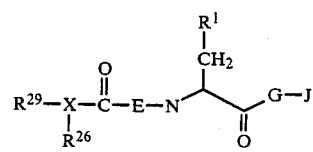

wherein X is

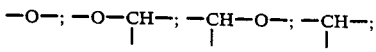

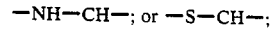

R$^1$ is hydrogen, C$_1$-C$_4$-alkyl, hydroxy-C$_1$-C$_4$-alkyl, aryl, as defined below, indolyl, 4-imidazolyl, amino-C$_2$-C$_4$-alkyl, Guanidyl-C$_2$-C$_3$-alkyl or methylthiomethyl; R$^{29}$ and R$^{26}$ are independently hydrogen, or W-(CH$_2$)n in which W is hydrogen, C$_1$-C$_4$-alkyl, aryl, wherein aryl is unsubstituted or mono-, di or trisubstituted phenyl or naphthyl where each substituent is independently selected from the group consisting of C$_1$-C$_8$-alkyl, amino, mono-or di-C$_1$-C$_4$-alkylamino, amino-C$_1$-C$_4$-alkyl, hydroxy-C$_1$-C$_4$-aklyl, mono- or di-C$_1$-C$_4$-aklylamino-C$_1$-C$_4$-alkyl, guanidyl, guanidyl-C$_1$-C$_4$- alkoxy, CF₃, halo, CO₂H, CO₂-C₁-C₄-alkyl, CO₂-C₁-C₄-alkoxy, NR⁵R⁶, and N(R⁵)₊₃A−,
wherein R⁵ and R⁶ are independently hydrogen, unsubstituted C₁-C₄-alkyl, and A− is an anion, and n is 0 to 5; except that when X is —O— only one of R²⁹ or R²⁶ is present; E is absent; or

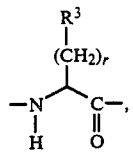

where r is 1 to 4; and
R³ is hydrogen; C₁-C₄-alky; aryl, as defined above; aryl-C₁-C₄-alkyl; or indolyl;

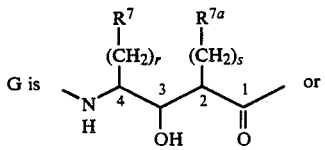

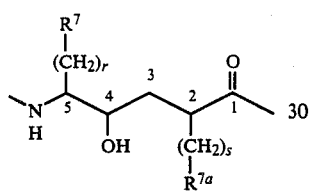

wherein R⁷ is C₃-C₆-alkyl; aryl, as defined above; or unsubstituted or mono-, di- or trisubstituted C₃-C₇-cycloalkyl, wherein each substituent is independently selected from the group consisting of C₁-C₄-alkyl, trifluoromethyl, hydroxy, C₁-C₄-alkoxy, and halo; and s is 0 to 4; R⁷ᵃ is hydrogen; C₁-C₈-alkyl; C₂-C₈-alkenyl; mono or disubstituted C₂-C₈-alkyl, wherein the substituent (s) is/are on the final 1 and/or 2 carbon atoms of the alkyl chain and is/are independently selected from the group consisting of hydroxy aryl, as defined above; unsubstituted or mono-, di- or trisubstituted C₃-C₇-cycloalkyl, wherein each substituent is independently selected from the group consisting of C₁-C₄-alkyl, trifluoromethyl, hydroxy, C₁-C₄-alkoxy, and halo; R⁷, X¹ and r are as defined above; and wherein the first alternate G definition of the above formula has a 2S or 2R, 3S, 4S configuration; and J is Y-(CH₂)x [CH(R⁵)]y-(CH₂)z-R¹⁰ wherein Y is oxygen, NH, or N-C₁-C₄-alkyl, x and y are independently zero, 1, 2, or 3 and z is zero or one; R¹⁰ is a quarternized 5 to 7 membered heterocyclic ring containing N⁺A⁻; quaternized ring containing one additional heteroatom selected from N, NO, O, S, SO or SO₂; a quaternized ring as defined containing a substituent on the ring carbon in which the substituent on the ring carbon in which the substituent is selected from —OH, —CO₂H, —SO₃H, —SO₂NH₂, -aryl as defined above, —CF₃, —halo, or unsubstituted mono, or di-C₁-C₄-alkylamino; a quaternized ring as defined in which the nitrogen is substituted by R¹¹ and R¹² as defined below; or the quaternized nitrogen is fused with a second ring having 4 to 6 carbon atoms forming a spiro-fused ring system, or fused with a —(CH₂)₂—O—(CH₂)₂— substituent;

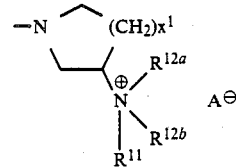

in which x1 is 1, 2 or 3;

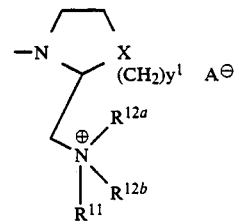

in which Y¹ is zero or 1 and X is absent, oxygen or NH;

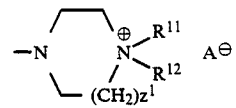

in which Z¹ is 1 or 2, A— is an anion, and R¹²ᵃ and R¹²ᵇ have the same significance as R¹²; R¹¹ is C₁-C₄ alkyl, substituted C₁-C₄ alkyl in which the substituent is —OH, —CO₂H, —SO₃H, —SO₂NH₂, -aryl as defined above, -halo, unsubstituted, mono or di-C₁-C₄ alkylamino-; a non-quaternized 5 or 6 membered heterocyclic ring containing a nitrogen and an additional heteroatom selected from N, NO, O, S, SO₂ or SO₂, or a 5 or 6 memebered heterocyclic ring containing one nitrogen and one additional heteroatom as defined and substituted with one or two C₁-C₄ alkyl; R¹² is C₁-C₄ alkyl; and, -NR¹¹R¹²ᵃR¹²ᵇ+A— in which R¹¹ is as defined above and R¹²ᵃ and R¹²ᵇ independently have the same significance as R¹² and A— is as defined above.

2. A compound according to claim 1 selected from the group consisting of:
[BOC-Phe-His-ACHPA-N(CH₂CH₂)₂NEt₂]+Cl−,
[BOC-Phe-His-ACHPA-NH(1,1-diethylpiperidonium-4-yl)]+Cl−,
[BOC-Phe-His-ACHPA-NHCH₂CH₂(1,1diethylpiperidin-4-yl)]+Cl−,
[BOC-Phe-His-ACHPA-NHCH₂CH₂(4-ethylmorpholinium-4-yl)]+Cl−,
[BOC-Phe-His-ACHPA-NH(1-methylquinuclidin-4-yl)]+Cl−,
[BOC-Phe-His-ACHPA-NH(1-(4-hydroxybutyl)quinuclidin-3-yl)]+Cl−,
[BOC-Phe-His-ACHPA-NH(1,1-dimethylpiperidin-3-yl)]+Cl−,
[IPOC-Phe-His-ACHPA-NH(1,1-dimethylpiperidin-3-yl)]+Cl−,
[IPOC-Phe-His-ACHPA-NH(1,1-dimethylpiperidin-4-yl)]+I−,
[BOC-Phe-His-ACHPA-NH-CH(2-butyl)-CH₂-N(CH₃)(CH₂CH₂)₂O]+Cl−,
[BOC-Phe-His-ACHPA-NH-CH(2-butyl)-CH₂−N(CH₃)(CH₂CH₂)₂-NHCH₃]+Cl−,

[BOC-Phe-His-ACHPA-NH-CH(2-butyl)-CH$_2$-N(CH$_3$)(CH$_2$CH$_2$)$_2$SO$_2$]+Cl−,
[BOC-Phe-His-ACHPA-NH-CH(2-butyl)-CH$_2$-N(CH$_2$CH$_2$)$_2$N (CH$_3$)$_2$]+Cl−,
[BOC-Phe-His-ACHPA-NH-CH(2-butyl)-CH$_2$-N(CH$_3$)$_3$]+Cl−,
[BOC-Phe-His-ACHPA-N(i-propyl)-CH$_2$-N(CH$_3$)$_3$]+Cl−,
[BOC-Phe-His-ACHPA-N(CH$_3$)-CH(2-butyl)-CH$_2$-N(CH$_3$)$_3$]+Cl−,
[BOC-Phe-His-ACHPA-N(i-butyl)-CH(2-butyl)-CH$_2$-N(CH$_3$)$_3$]+Cl−,
[BOC-Phe-His-ACHPA-NH-CH(2-butyl)-CH$_2$-N(CH$_2$CH$_3$)$_3$]+Cl−,
[BOC-Phe-His-ACHPA-NH-CH(2-butyl)-CH$_2$-CH$_2$-N(CH$_2$CH$_3$)$_3$]+Cl−,
[BOC-Phe-His-ACHPA-NH-CH(2-butyl)-CH$_2$-CH$_2$-CH$_2$-N(CH$_2$CH$_3$)$_3$]+Cl−,
[BOC-Phe-His-ACHPA-NH-CH(2-butyl)-CH$_2$-NH-(1-ethylpyridinium-4-yl)]+Cl−,
[BOC-Phe-His-ACHPA-NH-CH(2-butyl)-CH$_2$-(1-methyl-3-oxopiperidinonium-1-yl)]+Cl−,
[BOC-Phe-His-ACHPA-NH-CH(2-butyl)-CH$_2$-NH-(1,1-dimethylpiperidinium-4yl)]+Cl−,
[BOC-Phe-His-ACHPA-NH-CH(2-butyl)-CH$_2$-NH-(1,1-dimethylazepinonium-3-yl)]+Cl−,
BOC-Phe-His-ACHPA-NH-CH(2-butyl)-CH$_2$-NH-(N-methylquinuclidinonium-3-yl)]+Cl−,
[BOC-Phe-His-ACHPA-NH-CH(2-butyl)-CH$_2$-NH-CH$_2$-CH$_2$-N (CH$_3$)(CH$_2$CH$_2$)$_2$O]+Cl−,
[BOC-Phe-His-ACHPA-NH-CH(i-butyl)-CH$_2$-N(CH$_2$CH$_2$)-$_2$N (CH$_3$)$_2$]+Cl−,
[BOC-Phe-His-ACHPA-NH-CH$_2$-CH(2-butyl)-N(CH$_2$CH$_3$)$_3$]+OAc−,
[BOC-Phe-His-ACHPA-NH-CH(2-butyl)-CH$_2$-(2-hydroxymethyl-1-methylprrolidinium-1-yl)]+Cl−,
BOC-Phe-His-ACHPA-NH-CH(2-butyl)-CH$_2$-(2-carboxy-1-methyl pyrrolidinium-1-yl) inner salt
[BOC-Phe-His-ACHPA-NH-CH(2-butyl)-CH$_2$-(2-trimethylammoniomethyl-pyrrolidin-1-yl)]+Cl−,
[BOC-Phe-His-ACHPA-NH-CH(2-butyl)-CH$_2$-N-(CH$_3$)$_2$]+CH$_2$CO$_2$−
[BOC-Phe-His-ACHPA-NH-CH(2-butyl)-CH(OH)-CH$_2$-N(CH$_3$)-(CH$_2$CH$_2$)$_2$O]+AOc−,
[BOC-Phe-His-ACHPA-NH-CH(2-butyl)-CH$_2$-(pyridinium-1-yl)]+Cl−
BOC-Phe-His-ACHPA-NH-CH(2-butyl)-CH$_2$-1-methylimidazolium-yl)]+Cl−,
BOC-Phe-His-ACHPA-NH-CH(2-butyl)-CH$_2$-N(CH$_3$)$_2$+CH$_2$CH$_2$CO$_2$−,
BOC-Phe-His-ACHPA-NH-CH(2-butyl)-CH$_2$-N(CH$_3$)$_2$+CH$_2$CH$_2$SO$_3$−,
[BOC-Phe-His-ACHPA-NH-CH(2-butyl)-CH$_2$-N(CH$_3$)$_2$CH$_2$CH$_2$OH]+Cl−,
[BOC-Phe-His-ACHPA-NH-CH(2-butyl)-CH$_2$-N(CH$_3$)$_2$CH$_2$CH$_2$ CH$_2$OH]+OAc−,
[BOC-Phe-His-ACHPA-NH-CH(2-butyl)-CH$_2$-N(CH$_3$)$_2$CH$_2$CH$_2$N(CH$_3$)$_2$]+OAc−,
[BOC-Phe-His-ACHPA-NH-CH(2-butyl)-CH$_2$-NH-CH$_2$CH$_2$N(CH$_3$)$_3$]+Cl−,
BOC-Phe-His-ACHPA-NH-CH(2-butyl)-CH$_2$-NH-CH$_2$CH(CO$_2$)-N(CH$_3$)$_3$+,
[BOC-Phe-His-ACHPA-N(i-butyl)-CH$_2$-CH$_2$-N(CH$_3$)(CH$_2$CH$_2$)$_2$O]+Cl−,
[BOC-Phe-His-ACHPA-N(i-butyl)-CH$_2$-CH$_2$-N(CH$_2$CH$_2$)(CH$_3$)$_2$]+Cl−,
[BOC-Phe-His-ACHPA-N(i-butyl)-CH$_2$-CH$_2$-N(CH$_3$)$_3$]+Cl−,
BOC-Phe-His-ACHPA-N(i-butyl)-CH$_2$-CH$_2$-N(CH$_3$)$_2$+CH$_2$CO$_2$−,
BOC-Phe-His-Cal[CH(OH)CH$_2$]Val-NH-CH$_2$CH$_2$N(CH$_2$CH$_2$)$_2$N (CH$_3$)$_2$+Cl−,
BOC-Phe-His-Cal[CH(OH)CH$_2$]val-NH-CH(2-butyl)-CH$_2$-N (CH$_3$)$_3$+Cl−,
BOC-Phe-His-Cal[CH(OH)CH$_2$]Val-NH-CH$_2$(1-methylpyridinium4-yl)+Cl−,
[BOC-Phe-His-Cal[CH(OH)CH$_2$]Val-NH-CH$_2$(1-methylpyridinium2-yl)]+Cl−,
BOC-Phe-His-Cal[CH(OH)CH$_2$]Val-NH-CH$_2$(4-trimethylammoniophenyl)]+Cl−,
[N-(4-trimethylammoniophenyl)Phe-His-Cal[CH(OH)CH$_2$]Val-NH-(2(S)-methylbutyl)]+Cl−, and
[Dibenzylacetyl-His-Cal[CH(OH)CH$_2$]Val-NH-CH$_2$CH$_2$N(CH$_2$CH$_2$) $_2$N(CH$_3$)$_2$]+Cl−.

3. A tripeptide according to claim 2, selected from the group consisting of: Boc-Phe-His-ACHPA-NH-[1-(4-hydroxylbutyl)quinuclidinium-3-yl] acetate; Boc-Phe-His-ACHPA-NH[1-(2-pyridylmethyl)-quinuclidinium-3-yl] acetate; Boc-Phe-His-ACHPA-NH-(1-methylquinuclidinyl-3-yl) acetate; [Boc-Phe-His-ACHPA-NH-CH(2-butyl)CH$_2$-N(CH$_3$) (CH$_2$CH$_2$)$_2$O]⊕acetate⊖; [Boc-Phe-His-ACHPA-NH-CH(2-butyl)-CH$_2$N(CH$_3$)(CH$_2$CH$_2$)$_2$NCH$_3$]⊕ OAc⊖; [Boc-Phe-His-ACHPA-NH-CH(2-butyl)-CH$_2$ NH(CH$_2$CH$_2$)$_2$N(CH$_3$)$_2$]⊕OAc⊖; Boc-Phe-His-ACHPA-NH-CH(2-butyl)-CH$_2$-N(CH$_3$)$_3$⊕Cl⊖; [Boc-Phe-His-ACHPA-NH-CH(2-butyl)-CH$_2$-NH-(1,1-dimethylazepinonnium-3-yl)]⊕cl⊖; and [Boc-Phe-His-ACHPA-NH-CH(2-butyl)-CH$_2$-N(CH$_3$)$_2$-CH$_2$ph]⊕acetate⊖.

4. Boc-Phe-His-ACHPA-NH-[1-(hydroxybutyl)-quinuclidinium-3-yl]acetate.

5. A pharmaceutical composition for treating renin-associated hypertension or congestive heart failure comprising a pharmaceutical carrier and a therapeutically-effective amount of a compound according to claim 1.

6. A pharmaceutical composition according to claim 5, also comprising an adjuvant.

7. A method of treating renin-associated hypertension or congestive heart failure in mammals comprising administering a therapeutically-effective amount of a compound according to claim 1.

8. A method according to claim 7, wherein the mammals are humans and the therapeutically-effective amount is from 0.02 to 10 grams per day.

* * * * *